(12) United States Patent
Nilsson

(10) Patent No.: US 11,559,615 B2
(45) Date of Patent: Jan. 24, 2023

(54) APPARATUS FOR EXTRACORPOREAL BLOOD TREATMENT

(71) Applicant: GAMBRO LUNDIA AB, Lund (SE)

(72) Inventor: Anders Nilsson, Södra Sandby (SE)

(73) Assignee: Gambro Lundia AB, Lund (SE)

( * ) Notice: Subject to any disclaimer, the term of this patent is extended or adjusted under 35 U.S.C. 154(b) by 713 days.

(21) Appl. No.: 16/470,095

(22) PCT Filed: Nov. 30, 2017

(86) PCT No.: PCT/EP2017/081064
§ 371 (c)(1),
(2) Date: Jun. 14, 2019

(87) PCT Pub. No.: WO2018/114276
PCT Pub. Date: Jun. 28, 2018

(65) Prior Publication Data
US 2019/0365977 A1 Dec. 5, 2019

(30) Foreign Application Priority Data
Dec. 22, 2016 (SE) .................................. 1651718-7

(51) Int. Cl.
*A61M 1/16* (2006.01)
*A61M 1/34* (2006.01)
(Continued)

(52) U.S. Cl.
CPC ........ *A61M 1/1607* (2014.02); *A61M 1/1656* (2013.01); *A61M 1/267* (2014.02);
(Continued)

(58) Field of Classification Search
CPC .............. A61M 1/1605; A61M 1/1607; A61M 1/1656; A61M 1/267; A61M 1/301;
(Continued)

(56) References Cited

U.S. PATENT DOCUMENTS

| 6,123,847 | A | 9/2000 | Bene |
| 6,156,002 | A | 12/2000 | Polaschegg et al. |

(Continued)

FOREIGN PATENT DOCUMENTS

| CN | 102378636 | 3/2012 |
| CN | 103547300 | 1/2014 |

(Continued)

OTHER PUBLICATIONS

Search Report for Chinese App. No. 201780080065.3 received Sep. 16, 2021 (3 pages).

(Continued)

*Primary Examiner* — Dirk R Bass
(74) *Attorney, Agent, or Firm* — K&L Gates LLP

(57) ABSTRACT

An extracorporeal blood treatment apparatus is provided comprising a filtration unit (2) connected to a blood circuit (17) and to a dialysate circuit (32), a preparation device (9) for preparing and regulating the composition of the dialysis fluid; a control unit (12) is configured for receiving a conductivity or sodium concentration set point for the dialysis fluid and for calculating a mass transport of a substance at an instant t of a treatment session based on said set value of the parameter for the dialysis fluid in the dialysis supply line (8).

18 Claims, 1 Drawing Sheet

(51) Int. Cl.
*A61M 1/26* (2006.01)
*A61M 1/30* (2006.01)
*G16H 20/40* (2018.01)

(52) U.S. Cl.
CPC .......... *A61M 1/301* (2014.02); *A61M 1/3406* (2014.02); *A61M 1/3413* (2013.01); *G16H 20/40* (2018.01); *A61M 2205/18* (2013.01); *A61M 2205/3317* (2013.01); *A61M 2205/3337* (2013.01); *A61M 2230/20* (2013.01)

(58) Field of Classification Search
CPC .............. A61M 1/3406; A61M 1/3413; A61M 1/3437; A61M 2205/18; A61M 2205/3317; A61M 2205/3337; A61M 2230/20; A61M 2230/65; G16H 20/40
See application file for complete search history.

(56) References Cited

U.S. PATENT DOCUMENTS

| | | | |
|---|---|---|---|
| 6,217,539 | B1 | 4/2001 | Goldau |
| 6,702,774 | B1 | 3/2004 | Polaschegg |
| 2001/0037968 | A1 | 11/2001 | Bene et al. |
| 2009/0221948 | A1 | 9/2009 | Szamosfalvi et al. |
| 2010/0105990 | A1 | 4/2010 | Bene |
| 2011/0079558 | A1 | 4/2011 | Raimann et al. |
| 2011/0237996 | A1 | 9/2011 | Kotanko et al. |
| 2012/0018379 | A1 | 1/2012 | Gross et al. |
| 2012/0273354 | A1 | 11/2012 | Orhan et al. |
| 2013/0116650 | A1* | 5/2013 | Vantard ............... A61M 1/1647 604/506 |
| 2014/0042092 | A1 | 2/2014 | Akonur et al. |

FOREIGN PATENT DOCUMENTS

| | | |
|---|---|---|
| EP | 0547025 | 6/1993 |
| EP | 1389475 | 2/2004 |
| WO | 2011/026646 | 3/2011 |
| WO | 2011/132046 | 10/2011 |
| WO | 2014/121161 | 8/2014 |
| WO | 2016/188951 | 12/2016 |
| WO | 2016/188952 | 12/2016 |

OTHER PUBLICATIONS

Chinese Office Action for App. No. 201780080065.3 dated Aug. 4, 2021 (18 pages).

* cited by examiner

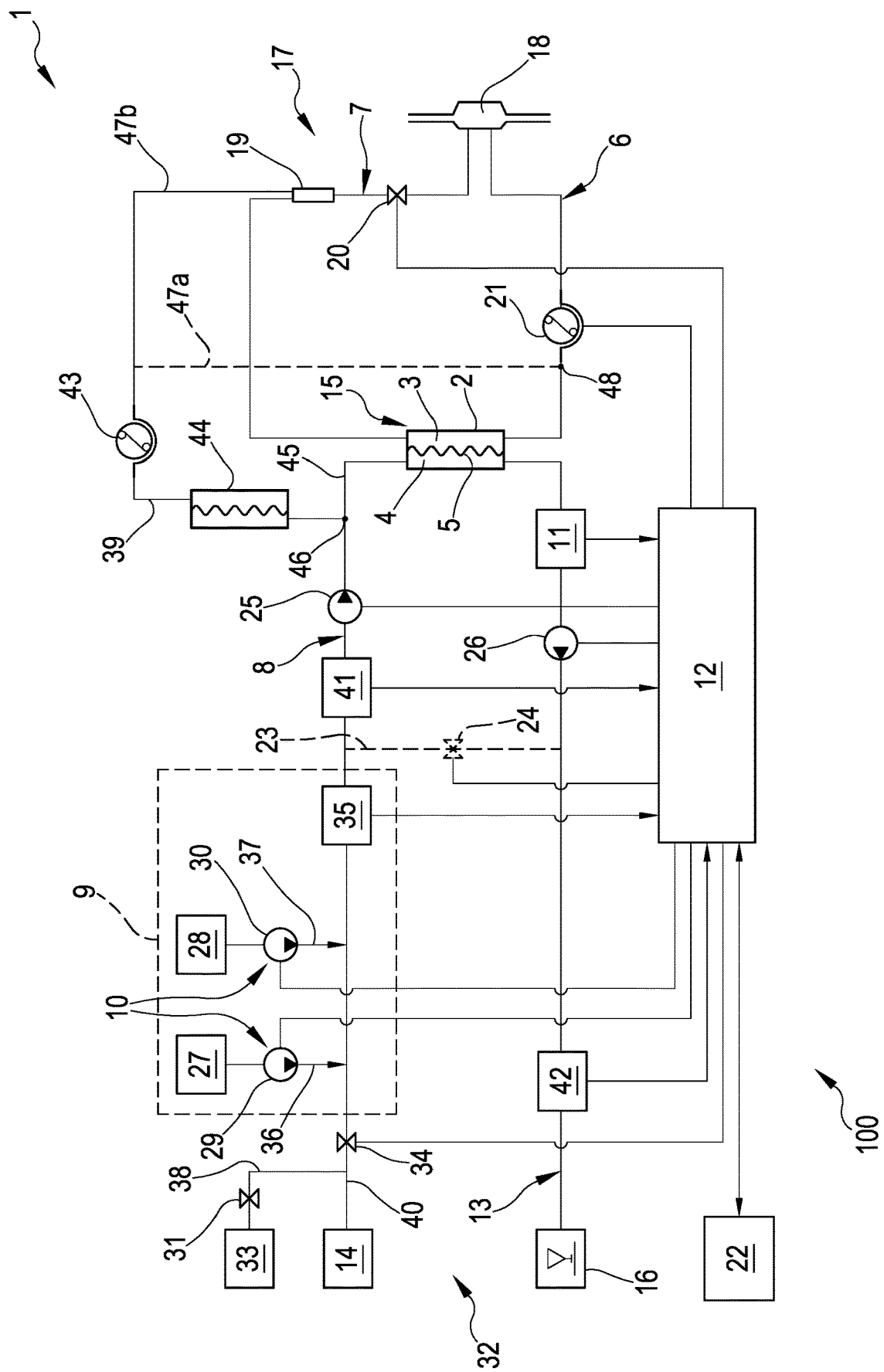

APPARATUS FOR EXTRACORPOREAL BLOOD TREATMENT

PRIORITY CLAIM

The present application is a National Phase entry of International Application No. PCT/EP2017/081064, filed Nov. 30, 2017, which claims priority to Swedish Application No. 1651718-7, filed Dec. 22, 2016, the entire contents of each of which are incorporated herein by reference and relied upon.

TECHNICAL FIELD

The present invention relates to an apparatus for extracorporeal blood treatment and a method for controlling the extracorporeal blood treatment apparatus.

In particular, the invention allows achieving a desired substance transport to, or from, the patient during the treatment.

Additionally, the invention may allow determining the substance transport (e.g. sodium) to or from the patient after a certain lapsed time of the treatment.

The invention may be used for regulating the conductivity of a dialysis liquid during a hemodialysis treatment.

In more detail, the apparatus and the method are particularly adapted for properly regulating the concentration of sodium in the dialysis liquid, particularly to achieve a chosen diffusive sodium mass transport over the treatment and/or to determine the diffusive sodium mass transport over the treatment.

BACKGROUND OF THE INVENTION

The kidneys fulfil many functions, including the removal of water, the excretion of catabolites (or waste from the metabolism, for example urea and creatinine), the regulation of the concentration of the electrolytes in the blood (e.g. sodium, potassium, magnesium, calcium, bicarbonates, phosphates, chlorides) and the regulation of the acid/base equilibrium within the body, which is obtained in particular by the removal of weak acids and by the production of ammonium salts.

In individuals who have lost the use of their kidneys, since these excretion and regulation mechanisms no longer work, the body accumulates water and waste from the metabolism and exhibits an excess of electrolytes, as well as, in general, acidosis, the pH of the blood plasma shifting downwards, below 7.35 (the blood pH normally varies within narrow limits of between 7.35 and 7.45).

In order to overcome renal dysfunction, resort is conventionally made to a blood treatment involving extracorporeal circulation through an exchanger having a semipermeable membrane (dialyzer) in which the patient's blood is circulated on one side of the membrane and a dialysis liquid, comprising the main electrolytes of the blood in concentrations close to those in the blood of a healthy subject, is circulated on the other side.

Furthermore, a pressure difference is created between the two compartments of the dialyzer which are delimited by the semipermeable membrane, so that a fraction of the plasma fluid passes by ultrafiltration through the membrane into the compartment containing the dialysis liquid.

The blood treatment which takes place in a dialyzer as regards waste from the metabolism and electrolytes results from two mechanisms of molecular transport through the membrane.

On the one hand, the molecules migrate from the liquid where their concentration is higher to the liquid where their concentration is lower. This is diffusive transport.

On the other hand, certain catabolites and certain electrolytes are entrained by the plasma fluid which filters through the membrane under the effect of the pressure difference created between the two compartments of the exchanger. This is convective transport.

Three of the abovementioned functions of the kidney, namely the removal of water, the excretion of catabolites and the regulation of the electrolytic concentration of the blood, are therefore performed in a conventional blood treatment device by the combination of dialysis and blood filtration (this combination is referred to as hemodialysis).

As regards the regulation of the acid/base equilibrium inside the body, the approach adopted to overcome renal deficiency is to act on a mechanism by which the acid/base equilibrium inside the body is regulated, this mechanism consisting of the buffer systems of the blood, the main one of which comprises carbonic acid, as a weak acid, associated with its alkali salt, bicarbonate. This is why, in order to correct acidosis in a patient suffering from renal insufficiency, he is administered with bicarbonate via the vascular route, directly or indirectly, during a hemodialysis session.

Moreover, it must be underlined that sodium is the main ionic solute of extracellular volume. From literature search and according to the main opinion leaders in the dialysis field, the determination of dialysis fluid sodium concentration to be used during the dialysis treatment appears as one of the major challenges of dialysis prescription.

The dialysis fluid sodium concentration significantly affects the sodium balance and the intracellular hydration of the patient with implications on hemodialysis tolerance and also long term patient survival.

Hypertonic dialysis fluid sodium prescription will result in a positive sodium balance followed by a water shift from the intracellular to extracellular compartment. The intracellular dehydration increases vasopressin release and provokes thirst with the consequence of a greater inter-dialytic weight gain and hypertension.

On the contrary, a dialysis fluid sodium concentration that is too low (i.e., hypotonic) will provoke a negative sodium gradient with a water shift in the intracellular compartment, which is responsible for intra-dialytic cramps, headache, hypovolemia and risk of hypotension.

As above mentioned, sodium is removed during dialysis through convection and diffusion. The main sodium removal process during dialysis is convective. If we assume that the ultrafiltrate fluid is basically isotonic, convection does not change the tonicity of the extracellular fluid.

There are two fundamental ways to evaluate the physiological effects of substance transport from or to the patient during a dialysis treatment.

The first way is the idea of an ideal plasma concentration of a substance that represents a homeostatic state. To achieve that plasma concentration a corresponding dialysis fluid setting is selected and the dialysis process drives the plasma concentration towards the desired concentration.

The prior art devices include dialysis apparatus wherein the conductivity of dialysis fluid is controlled in order to reach a desired post-dialysis plasmatic conductivity, i.e. conductivity (or sodium concentration) of the patient's blood at the end of the dialysis treatment.

It is known, for example from EP 1389475, a dialysis apparatus provided with a conductivity system that computes the dialysis fluid conductivity (corresponding to the dialysis fluid sodium concentration) from periodic measurements of the sodium blood concentration allowing the sodium level of the patient to reach a prescribed end-of-session value.

This dialysis apparatus includes a bag and a pump for infusing a patient with an infusion solution containing sodium at a determined and known concentration.

A structure for determining the sodium concentration $[Na^+]_{dial}$ of the dialysis liquid is also provided so that the patient's body tends towards a desired sodium concentration $[Na^+]_{des}$, as a function of the dialysance D for sodium of the dialyser, of the desired sodium concentration $[Na^+]_{des}$ inside the patient's body, of the infusion flow rate and of the sodium concentration $[Na^+]_{sol}$ of the infusion solution. A control unit drives the pump for regulating the sodium concentration of the dialysis liquid such that this concentration is equal (tends towards) to the determined concentration $[Na^+]_{dial}$.

The second way to evaluate the physiological effects of substance transport from or to the patient during a dialysis treatment and to quantify the effect is to study the mass balance or dose the treatment causes. This will in the long run match the net intake by food for the substance.

Regarding sodium it is more beneficial to know the mass balance rather than its concentration as it is the total mass of sodium that distributes water between extracellular and intracellular space. A homeostatic volume of the extracellular space is crucial for heart function and blood pressure control. The plasma sodium concentration itself is not linked to the extracellular volume.

As previously mentioned, one of the problems of the dialysis apparatus of the discussed prior art is presently the choice of the appropriate post-dialysis plasmatic conductivity target.

Also the proper monitoring of the achieved mass transport after a certain time period t of the treatment is a valuable parameter to provide to the physician.

There is no sodium balance measuring/control device on the market today.

SUMMARY

An aim of the present invention is providing an extracorporeal blood treatment apparatus able to automatically perform a proper setting of the dialysis fluid content of a substance, particularly an ionic substance, present in the blood as well.

In detail it is an aim of the present invention to provide an extracorporeal blood treatment apparatus with a proper tool helping the physician to set a desired mass transport and prescribe a dialysis fluid composition, particularly suitable to achieve the desired mass transport at the end of the dialysis treatment.

A further aim of the invention is to make available an extracorporeal blood treatment apparatus configured to achieve a specified non-zero transport by adding a proper term to an isonatric setting.

Moreover, it is an aim to provide a tool allowing the extracorporeal blood treatment apparatus to determine and/or monitor the achieved substance mass transport during the treatment delivery (e.g. after the elapse of a certain treatment time t).

A further aim of the invention is to make available an extracorporeal blood treatment apparatus which is easy to use and designed for not skilled operators or users working in crowded and busy dialysis rooms.

It is an aim of the invention to provide an extracorporeal blood treatment machine configured to automatically perform a proper automatic setting of the dialysis fluid conductivity.

A further aim of the invention is to make available a dialysis apparatus able to provide an automated delivery and control of the dialysis prescription, particularly in order to restore at each dialysis session the proper sodium-water equilibrium to the patient.

At least one of the above-indicated aims is attained by an apparatus and a corresponding method as in one or more of the appended claims, taken singly or in any combination.

According to a first independent aspect of the invention an extracorporeal blood treatment device is provided including:
  a filtration unit (2) having a primary chamber (3) and a secondary chamber (4) separated by a semi-permeable membrane (5);
  a blood withdrawal line (6) connected to an inlet of the primary chamber (3),
  a blood return line (7) connected to an outlet of the primary chamber (3), said blood lines being configured for connection to a patient cardiovascular system;
  a dialysis supply line (8);
  a dialysis effluent line (13) connected to an outlet of the secondary chamber (4);
  a preparation device (9) for preparing a dialysis fluid connected to said supply line (8) and comprising regulating means (10) for regulating the composition of the dialysis fluid,
  a control unit (12) connected to the regulating means (10) and programmed for receiving a desired mass transport of a substance at the end of a treatment session and a value representative of a first parameter, the first parameter being chosen in the group including a plasma conductivity, a plasma conductivity-related parameter, a concentration of the substance in the blood, a concentration-related parameter of the substance in the blood, a conductivity of the dialysis fluid, a conductivity-related parameter of the dialysis fluid, a concentration of the substance in the dialysis fluid and a concentration-related parameter of the substance in the dialysis fluid, wherein said control unit (12) is configured for setting a second parameter value for the dialysis fluid in the dialysis supply line (8) at a set point, said second parameter of the dialysis fluid being at least one chosen in a group including a conductivity of the dialysis fluid, a conductivity-related parameter of the dialysis fluid, a concentration of the substance in the dialysis fluid and a concentration-related parameter of the substance in the dialysis fluid;
wherein the setting of the second parameter value in the dialysis fluid includes the sub-step of calculating the second parameter value as a function of the desired mass transport.

In a further independent aspect a method for setting parameters in an apparatus for extracorporeal blood treatment is provided, the apparatus comprising:
  a filtration unit (2) having a primary chamber (3) and a secondary chamber (4) separated by a semi-permeable membrane (5);
  a blood withdrawal line (6) connected to an inlet of the primary chamber (3),
  a blood return line (7) connected to an outlet of the primary chamber (3), said blood lines being configured for connection to a patient cardiovascular system;
  a dialysis supply line (8);
  a dialysis effluent line (13) connected to an outlet of the secondary chamber (4);

a preparation device (9) for preparing a dialysis fluid connected to said supply line (8) and comprising regulating means (10) for regulating the composition of the dialysis fluid, a control unit (12) connected to the regulating means (10) and programmed for receiving a desired mass transport of a substance at the end of a treatment session and a value representative of a parameter of the blood in said blood lines (6, 7), the blood related parameter being chosen in the group including a plasma conductivity, a plasma conductivity-related parameter, a concentration of the substance in the blood, a concentration-related parameter of the substance in the blood, a conductivity of the dialysis fluid, a conductivity-related parameter of the dialysis fluid, a concentration of the substance in the dialysis fluid and a concentration-related parameter of the substance in the dialysis fluid, the method comprising the following steps performed by the control unit:

setting a second parameter value for the dialysis fluid in the dialysis supply line (8) at a set point, said second parameter of the dialysis fluid being at least one chosen in a group including a conductivity of the dialysis fluid, a conductivity-related parameter of the dialysis fluid, a concentration of the substance in the dialysis fluid and a concentration-related parameter of the substance in the dialysis fluid;

wherein the setting of the second parameter value in the dialysis fluid includes the sub-step of calculating the second parameter value as a function of the desired mass transport.

In a $2^{nd}$ aspect according to anyone of the previous aspects, the control unit is configured to calculate the second parameter value as a function of a main contribution term based on the first parameter and as a function of an adjustment contribution term function of the desired mass transport.

In a $3^{rd}$ aspect according to the previous aspect, the main contribution term is dimensionally a concentration of a substance in a fluid.

In a $4^{th}$ aspect according to anyone of the previous aspects 2 and 3, the main contribution term is a dialysis fluid concentration of a substance at a dialysis treatment where the substance concentration of the dialysis fluid does not change pre- to post-filtration unit (2), in particular the main contribution term is a dialysis fluid concentration of sodium at an isonatric dialysis.

In a $5^{th}$ aspect according to anyone of the previous aspects 2 to 4, the control unit is configured to calculate the adjustment contribution term as a function of an efficiency parameter of the filtration unit (2) for the substance, in particular the clearance of the substance.

In a $6^{th}$ aspect according to anyone of the previous aspects 2 to 5, the control unit is configured to calculate the adjustment contribution term as a function of a patient distribution volume of the substance, optionally the control unit is configured to calculate the adjustment contribution term as a function of a respective adjusting factor taking account of the Donnan effect In a $7^{th}$ aspect according to anyone of the previous aspects 2 to 6, the control unit is configured to calculate the adjustment contribution term as a function of a treatment time, in particular the total treatment time.

In a $8^{th}$ aspect according to anyone of the previous aspects 2 to 7, the control unit is configured to calculate the adjustment contribution term as a function of an ultrafiltration rate and/or an expected total ultrafiltered volume.

In a $9^{th}$ aspect according to anyone of the previous aspects, the control unit is configured to calculate the second parameter value as a function of an efficiency parameter of the filtration unit (2) for the substance, in particular the clearance of the substance.

In a $10^{th}$ aspect according to anyone of the previous aspects, the control unit is configured to calculate the second parameter value as a function of a distribution volume of the substance.

In an $11^{th}$ aspect according to anyone of the previous aspects, the control unit is configured to calculate the second parameter value as a function of a treatment time, in particular the total treatment time, optionally the control unit is configured to calculate the second parameter value as a function of a respective adjusting factor taking account of the Donnan effect.

In a $12^{th}$ aspect according to anyone of the previous aspects, the control unit is configured to calculate the second parameter value as a function of an ultrafiltration rate and/or an expected total ultrafiltered volume.

In a $13^{th}$ aspect according to anyone of the previous aspects, the first parameter is a blood related parameter chosen between the plasma conductivity, or the concentration of the substance in the blood, said substance being in particular sodium.

In a $14^{th}$ aspect according to the previous aspect, the parameter of the dialysis fluid is the conductivity of the dialysis fluid, or the concentration of the substance in the dialysis fluid, said substance being in particular sodium.

In a $15^{th}$ aspect according to anyone of the previous aspects, the first parameter is the plasma conductivity and the parameter of the dialysis fluid is the conductivity of the dialysis fluid.

In a $16^{th}$ aspect according to anyone of the previous aspects, the first parameter is the concentration of the substance in the blood, said substance being in particular sodium, and wherein the parameter of the dialysis fluid is the concentration of the substance in the dialysis fluid, said substance being in particular sodium.

In a $17^{th}$ aspect according to anyone of the previous aspects, the first parameter is a substance concentration which, if applied as dialysis fluid concentration of sodium, would provide isonatric dialysis.

In a $18^{th}$ aspect according to anyone of the previous aspects from 2 to 8, the sub-step of calculating the parameter value as a function of the main contribution term and the adjustment contribution term is a sub-step of calculating an algebraic sum of at least the main contribution term and the adjustment contribution term and particularly wherein the adjustment contribution term is dimensionally a concentration of a substance in a fluid.

In a $19^{th}$ aspect according to anyone of the previous aspects 2 to 8, the adjustment contribution term is the sodium concentration set point adjustment relative to an isonatric dialysis to provide a treatment configured to achieve the desired total or diffusive mass transport over the treatment time.

In a $20^{th}$ aspect according to anyone of the previous aspects, the sub-step of calculating the second parameter value is a sub-step of calculating the second parameter value to achieve the desired diffusive or total mass transport over the treatment time.

In a $21^{st}$ aspect according to anyone of the previous aspects, the first parameter is a parameter representative of an isoconductive dialysis, e.g. either a concentration of a substance in the dialysis fluid which would provide an isoconductive dialysis or a conductivity of the dialysis fluid which would provide an isoconductive dialysis.

In a 22$^{nd}$ aspect according to anyone of the previous aspects, the control unit drives the regulating means (10) for regulating the conductivity or the concentration of at least a substance in the dialysis fluid, the control unit setting the second parameter value for the dialysis fluid in the dialysis supply line (8) at the calculated set point.

In a 23$^{rd}$ aspect according to anyone of the previous aspects, the regulating means (10) regulates the concentration of the substance in the dialysis fluid, in particular an ionic substance, such as sodium.

In a 24$^{th}$ aspect according to anyone of the previous aspects, the control unit drives the regulating means (10) for regulating the sodium concentration in the dialysis fluid to set the parameter value for the dialysis fluid in the dialysis supply line (8) at the calculated set point.

In a 25$^{th}$ aspect according to anyone of the previous aspects, the control unit (12) is programmed for calculating said value representative of the first parameter.

In a 26$^{th}$ aspect according to anyone of the previous aspects, the control unit (12) is programmed for receiving as an input said first parameter.

In a 27$^{th}$ aspect according to anyone of the previous aspects, the control unit (12) is programmed for storing in a memory said value representative of the first parameter, said first parameter being not calculated by the control unit.

In a 28$^{th}$ aspect according to anyone of the previous aspects 2 to 8, the adjustment contribution term has a positive or negative value exclusively depending on the sign of the desired total or diffusive mass transfer.

In a 29$^{th}$ aspect according to anyone of the previous aspects, the control unit (12) is programmed for calculating the second parameter value according to the following relationship:

$$c_{d,M_d} = c_{d,isoNa} + \frac{\alpha \cdot M_d}{V_0 \cdot \left(e^{\frac{\alpha \cdot K_u}{V_0} \cdot T} - 1\right)} \quad \text{(I)}$$

wherein:

| | |
|---|---|
| $c_{d,M_d}$ | Dialysis fluid sodium concentration to achieve a desired diffusive sodium mass transfer at the treatment time T; |
| $c_{d,isoNa}$ | Dialysis fluid concentration of sodium at an isonatric dialysis; |
| $M_d$ | Desired mass transport of sodium; |
| $V_0$ | Initial distribution volume of sodium; |
| T | Total treatment time (set); |
| $K_u$ | Filtration unit clearance for sodium; |
| $\alpha$ | Donnan factor; |

In a 30$^{th}$ aspect according to anyone of the previous aspects 2 to 8, the adjustment contribution term is:

$$\frac{\alpha \cdot M_d}{V_0 \cdot \left(e^{\frac{\alpha \cdot K_u}{V_0} \cdot T} - 1\right)} \quad \text{(II)}$$

wherein:

| | |
|---|---|
| $M_d$ | Desired mass transport of sodium; |
| $V_0$ | Initial distribution volume of sodium; |
| T | Total treatment time (set); |
| $K_u$ | Dialyzer clearance for sodium; |
| $\alpha$ | Donnan factor; |

In a 31$^{st}$ aspect according to anyone of the previous aspects 1 to 28, the control unit (12) is programmed for calculating the second parameter value to achieve a desired total mass transport according to the following relationship:

$$c_{d,M} = c_{d,isoNa} + \frac{M - (V_2 - f_{cd} \cdot V_1) \cdot c_{d,isoNa}}{V_2 - (1 + f_{cd}) \cdot V_1} \quad \text{(III)}$$

wherein $f_{cd}$, $V_1$, $V_2$ and $V_u$ are:

$$f_{cd} = \frac{(1-\alpha) \cdot Q_u}{\alpha \cdot K_u - Q_u} \quad \text{(IV)}$$

$$V_1 = \frac{V_0}{\alpha} \cdot \left(1 - \left(1 - \frac{V_u}{V_0}\right)^{\frac{\alpha \cdot K_u}{Q_u}}\right) \quad \text{(V)}$$

$$V_2 = f_{cd} \cdot K_u \cdot T \cdot V_u \quad \text{(VI)}$$

$$V_u = Q_u \cdot T \quad \text{(VII)}$$

and wherein:

| | |
|---|---|
| $c_{d,M}$ | Dialysis fluid sodium concentration to achieve a desired total sodium mass transfer at the treatment time T; |
| $c_{d,isoNa}$ | Dialysis fluid concentration of sodium at an isonatric dialysis; |
| M | Desired total mass transport of sodium; |
| $V_0$ | Initial patient distribution volume of sodium; |
| $Q_u$ | Ultrafiltration rate; |
| T | Total treatment time (set); |
| $V_u$ | Expected total ultrafiltered volume; |
| $K_u$ | Filtration unit clearance for sodium; |
| $\alpha$ | Donnan factor; |

In a 32$^{nd}$ aspect according to anyone of the previous aspects, 2 to 8, the adjustment contribution term is:

$$\frac{M - (V_2 - f_{cd} \cdot V_1) \cdot c_{d,isoNa}}{V_2 - (1 + f_{cd}) \cdot V_1} \quad \text{(VIII)}$$

wherein $f_{cd}$, $V_1$, $V_2$ and $V_u$ are:

$$f_{cd} = \frac{(1-\alpha) \cdot Q_u}{\alpha \cdot K_u - Q_u} \quad \text{(IV)}$$

$$V_1 = \frac{V_0}{\alpha} \cdot \left(1 - \left(1 - \frac{V_u}{V_0}\right)^{\frac{\alpha \cdot K_u}{Q_u}}\right) \quad \text{(V)}$$

$$V_2 = f_{cd} \cdot K_u \cdot T \cdot V_u \quad \text{(VI)}$$

$$V_u = Q_u \cdot T \quad \text{(VII)}$$

and wherein:

| | |
|---|---|
| $c_{d,isoNa}$ | Dialysis fluid concentration of sodium at an isonatric dialysis; |
| M | Desired total mass transport of sodium; |
| $V_0$ | Initial patient distribution volume of sodium; |
| $Q_u$ | Ultrafiltration rate; |
| T | Total treatment time (set); |
| T | Set total treatment time; |
| $V_u$ | Expected total ultrafiltered volume; |
| $K_u$ | Filtration unit clearance for sodium; |
| $\alpha$ | Donnan factor; |

In a 33$^{rd}$ aspect according to anyone of the previous aspects 1 to 28, the control unit (12) is programmed for calculating the second parameter value to achieve a desired diffusive mass transport according to the following relationship:

$$c_{d,M_d} = c_{d,isoNa} + \frac{M_d - \left(V_2 - f_{cd} \cdot V_1 - \frac{V_u}{\alpha}\right) \cdot c_{d,isoNa}}{V_2 - (1 + f_{cd}) \cdot V_1} \quad \text{(IX)}$$

wherein $f_{cd}$, $V_1$, $V_2$ and $V_u$ are:

$$f_{cd} = \frac{(1-\alpha) \cdot Q_u}{\alpha \cdot K_u - Q_u} \quad \text{(IV)}$$

$$V_1 = \frac{V_0}{\alpha} \cdot \left(1 - \left(1 - \frac{V_u}{V_0}\right)^{\frac{\alpha \cdot K_u}{Q_u}}\right) \quad \text{(V)}$$

$$V_2 = f_{cd} \cdot K_u \cdot T \cdot V_u \quad \text{(VI)}$$

$$V_u = Q_u \cdot T \quad \text{(VII)}$$

wherein:

| | |
|---|---|
| $c_{d,M_d}$ | Dialysis fluid sodium concentration to achieve a desired diffusive sodium mass transfer at the treatment time T; |
| $c_{d,isoNa}$ | Dialysis fluid concentration of sodium at an isonatric dialysis; |
| $M_d$ | Desired diffusive mass transport of sodium; |
| $V_0$ | Initial patient distribution volume of sodium; |
| $Q_u$ | Ultrafiltration rate; |
| T | Total treatment time (set); |
| $V_u$ | Expected total ultrafiltered volume; |
| $K_u$ | Filtration unit clearance for sodium; |
| $\alpha$ | Donnan factor; |

In a 34$^{th}$ aspect according to anyone of the previous aspects 2 to 8, the adjustment contribution term is:

$$\frac{M_d - \left(V_2 - f_{cd} \cdot V_1 - \frac{V_u}{\alpha}\right) \cdot c_{d,isoNa}}{V_2 - (1 + f_{cd}) \cdot V_1} \quad \text{(X)}$$

wherein $f_{cd}$, $V_1$, $V_2$ and $V_u$ are:

$$f_{cd} = \frac{(1-\alpha) \cdot Q_u}{\alpha \cdot K_u - Q_u} \quad \text{(IV)}$$

$$V_1 = \frac{V_0}{\alpha} \cdot \left(1 - \left(1 - \frac{V_u}{V_0}\right)^{\frac{\alpha \cdot K_u}{Q_u}}\right) \quad \text{(V)}$$

$$V_2 = f_{cd} \cdot K_u \cdot T \cdot V_u \quad \text{(VI)}$$

$$V_u = Q_u \cdot T \quad \text{(VII)}$$

| | |
|---|---|
| $c_{d,isoNa}$ | Dialysis fluid concentration of sodium at an isonatric dialysis; |
| $M_d$ | Desired diffusive mass transport of sodium; |
| $V_0$ | Initial patient distribution volume of sodium; |
| $Q_u$ | Ultrafiltration rate; |
| T | Total treatment time (set); |
| $V_u$ | Expected total ultrafiltered volume; |
| $K_u$ | Filtration unit clearance for sodium; |
| $\alpha$ | Donnan factor; |

In a 35$^{th}$ aspect according to anyone of the previous aspects, the dialysis supply line (8) is connected to an inlet of the secondary chamber (4) to provide dialysis fluid to the filtration unit (2), the control unit (12) being configured to circulate dialysis fluid in the dialysis supply line (8) towards the filtration unit.

In a 36$^{th}$ aspect according to anyone of the previous aspects, the control unit is configured to calculate the plasma conductivity as a function of at least one flow rate, in particular said flow rate being chosen in the group including the dialysate flow rate at the outlet of the secondary chamber (4) and the blood flow rate in the blood lines (6, 7).

In a 37$^{th}$ aspect according to the previous aspect, the control unit is configured to calculate the plasma conductivity as a function of the dialysate flow rate at the outlet of the secondary chamber (4) and the blood flow rate in the blood lines (6, 7).

In a 38$^{th}$ aspect according to anyone of the previous aspects, the control unit is configured to calculate the plasma conductivity as a function of at least an efficiency parameter of the filtration unit (2), in particular a clearance of the filtration unit (2), optionally the urea clearance.

In a 39$^{th}$ aspect according to anyone of the previous aspects, the control unit is configured to calculate the plasma conductivity as a function of at least an initial conductivity of the dialysate.

In a 40$^{th}$ aspect according to anyone of the previous aspects, the control unit is configured to calculate the plasma conductivity as a function of at least a conductivity of the dialysis fluid in the dialysis supply line (8).

In a 41$^{st}$ aspect according to anyone of the previous aspects, the control unit is configured to calculate the plasma conductivity according to the following formula (V):

$$\kappa_{p,1} = \kappa_{0,di} + \frac{Q_{do}}{K_u}(\kappa_{0,do} - \kappa_{0,di}) \quad \text{(XI)}$$

wherein:

| | |
|---|---|
| $\kappa_{p,1}$ | Plasma conductivity first estimate; |
| $Q_{do}$ | Dialysate flow rate at the filtration unit outlet; |
| $K_u$ | Filtration unit clearance for urea; |

-continued

| $\kappa_{0,di}$ | Dialysis fluid conductivity at the filtration unit inlet for a pure electrolyte solution; |
| --- | --- |
| $\kappa_{0,do}$ | Dialysate conductivity at the filtration unit outlet for a pure electrolyte solution; |

In a 42$^{nd}$ aspect according to anyone of the previous aspects, immediately after calculating an initial plasma conductivity, the control unit is configured to drive the regulating means (10) to change the composition of the dialysis fluid and to set the dialysis fluid conductivity substantially equal to the calculated plasma conductivity.

In a 43$^{rd}$ aspect according to the previous aspect, after setting the dialysis fluid conductivity substantially equal to the calculated plasma conductivity, the control unit is configured to execute a second calculating step, based on a second determined initial conductivity of the dialysate and on a second corresponding conductivity of the dialysis fluid in the dialysis supply line (8), of a second estimate of the initial plasma conductivity, said calculating the second estimate being performed maintaining the dialysis fluid conductivity substantially constant and substantially equal to the calculated plasma conductivity.

In a 44$^{th}$ aspect according to anyone of the previous aspects, after calculating the second estimate of the initial plasma conductivity, the control unit is configured to drive the regulating means (10) to change the composition of the dialysis fluid and to set the dialysis fluid conductivity substantially equal to said second estimate plus an offset term to take into account of both an isonatric dialysis and the desired mass transport.

In a 45$^{th}$ aspect according to the previous aspect, the control unit is programmed to keep the desired dialysis fluid inlet conductivity substantially constant throughout the remainder of the treatment.

In a 46$^{th}$ aspect according to any of the previous aspects 37 to 45, the control unit is programmed to check whether the calculated plasma conductivity is within an acceptable safety range.

In a 47$^{th}$ aspect according to anyone of the previous aspects, the control unit is configured to propose the calculated set point to the user and to request confirmation prior driving the regulating means (10) for regulating the sodium concentration in the dialysis fluid to set the parameter value for the dialysis fluid in the dialysis supply line (8) at the calculated set point.

In a 48$^{th}$ aspect according to anyone of the previous aspects 2 to 8, the setting of the second parameter value in the dialysis fluid includes the sub-step of calculating the parameter value as a function of the main contribution term, the adjustment contribution term and a compensation contribution term.

In a 49$^{th}$ aspect according to the previous aspect, the compensation contribution term is dimensionally a concentration of a substance in a fluid.

In a 50$^{th}$ aspect according to anyone of the previous two aspects, the sub-step of calculating the parameter value as a function of the main contribution term, the adjustment contribution term and the compensation contribution term is a sub-step of calculating an algebraic sum of at least the main contribution term, the adjustment contribution term and the compensation contribution term.

In a 51$^{st}$ aspect according to anyone of the previous three aspects, the compensation contribution term is a sodium compensation term to compensate for occurred unwanted sodium transfers during treatment.

In a 52$^{nd}$ aspect according to anyone of the previous four aspects, the compensation contribution term is a sodium compensation term to compensate for unwanted sodium transfers occurred during calculation of said value representative of the parameter of the blood in said blood lines, particularly at the start of the treatment.

In a 53$^{rd}$ aspect according to the previous aspect, the compensation contribution term has generally a negative value.

In a 54$^{th}$ aspect according to anyone of the previous six aspects, the control unit (12) is further configured, during a monitoring phase, to re-determine the plasma conductivity, the monitoring phase occurring a predetermined number of times during the treatment, at each monitoring phase an unwanted net transfer of a substance, e.g. sodium, occurs through the semipermeable membrane (5), the compensation contribution term is a sodium compensation term to compensate for occurred unwanted sodium transfers during the monitoring phase.

In a 55$^{th}$ aspect according to anyone of the previous seven aspects, the compensation contribution term for the unwanted substance transfer is calculated for distributing a compensation for the substance during the remaining treatment time.

In a 56$^{th}$ aspect according to anyone of the previous eight aspects, the compensation contribution term is a function of the remaining treatment time, i.e. total treatment time (T) minus elapsed treatment time ($t_i$), in particular is a function of $$\frac{1}{T-t_i}.$$

In a 57$^{th}$ aspect according to anyone of the previous nine aspects, the compensation contribution term is a function of the difference between the calculated substance, e.g. sodium, set point ($c_{d,M_d}$) and the actual dialysis fluid same substance, e.g. sodium, concentration set point ($c_{d,Na,actual,i}$) used during treatment.

In a 58$^{th}$ aspect according to anyone of the previous ten aspects, the compensation contribution term is calculated according to the following formula:

$$\sum_i \frac{1}{T-t_i} \int_{t_i}^{t_i+\Delta t_i} (c_{d,M_d} - c_{d,Na,actual,i}) dt \qquad \text{(XII)}$$

wherein $c_{d,Na,actual,i}$ is the actual dialysis fluid sodium concentration set point used during the treatment;

$c_{d,M_d}$ is the calculated sodium set point which correspond to dialysis fluid concentration of sodium ions (Na$^+$) to provide the desired sodium mass transport $M_d$;

T is the total treatment time; and $t_i$ is the elapsed treatment time.

In a 59$^{th}$ aspect according to anyone of the previous eleven aspects, the second parameter value in the dialysis fluid is calculated according to the following relation:

$$c_{d,M_d,compensated} = c_{d,M_d} + \sum_i \frac{1}{T-t_i} \int_{t_i}^{t_i+\Delta t_i} (c_{d,M_d} - c_{d,Na,actual,i}) dt \qquad \text{(XIII)}$$

wherein:

$c_{d,M_d,compensated}$ is the dialysis fluid sodium concentration new set point to compensate for unwanted substance transfer;

$c_{d,Na,actual,i}$ is the actual dialysis fluid sodium concentration set point used during the treatment;

$c_{d,M_d}$ is the calculated sodium set point which correspond to dialysis fluid concentration of sodium ions (Na$^+$) to provide the desired sodium mass transport $M_d$;

T is the total treatment time; and $t_i$ is the elapsed treatment time.

In a 60$^{th}$ independent aspect, an apparatus for extracorporeal blood treatment is provided comprising:

a filtration unit (2) having a primary chamber (3) and a secondary chamber (4) separated by a semi-permeable membrane (5);

a blood withdrawal line (6) connected to an inlet of the primary chamber (3), a blood return line (7) connected to an outlet of the primary chamber (3), said blood lines being configured for connection to a patient cardiovascular system;

a dialysis supply line (8);

a dialysis effluent line (13) connected to an outlet of the secondary chamber (4);

optionally a preparation device (9) for preparing a dialysis fluid connected to said supply line (8) and comprising regulating means (10) for regulating the composition of the dialysis fluid, a control unit (12), in particular connected to the regulating means (10), and programmed for receiving a set value of a parameter for the dialysis fluid in the dialysis supply line (8), said parameter of the dialysis fluid being at least one chosen in a group including a conductivity of the dialysis fluid, a conductivity-related parameter of the dialysis fluid, a concentration of the substance in the dialysis fluid and a concentration-related parameter of the substance in the dialysis fluid;

wherein said control unit (12) is configured for calculating a mass transport of a substance at an instant t of a treatment session based on said set value of the parameter for the dialysis fluid in the dialysis supply line (8).

In a 61$^{st}$ independent aspect, a method for calculating a mass transport of a substance in an apparatus for extracorporeal blood treatment, the apparatus comprising:

a filtration unit (2) having a primary chamber (3) and a secondary chamber (4) separated by a semi-permeable membrane (5);

a blood withdrawal line (6) connected to an inlet of the primary chamber (3), a blood return line (7) connected to an outlet of the primary chamber (3), said blood lines being configured for connection to a patient cardiovascular system;

a dialysis supply line (8);

a dialysis effluent line (13) connected to an outlet of the secondary chamber (4);

optionally a preparation device (9) for preparing a dialysis fluid connected to said supply line (8) and comprising regulating means (10) for regulating the composition of the dialysis fluid, a control unit (12), in particular connected to the regulating means (10), and programmed for receiving a set value of a parameter for the dialysis fluid in the dialysis supply line (8), said parameter of the dialysis fluid being at least one chosen in a group including a conductivity of the dialysis fluid, a conductivity-related parameter of the dialysis fluid, a concentration of the substance in the dialysis fluid and a concentration-related parameter of the substance in the dialysis fluid;

the method comprising the following steps performed by the control unit:

receiving the set value of the parameter for the dialysis fluid in the dialysis supply line (8);

calculating a mass transport of a substance at an instant t of a treatment session based on said set value of the parameter for the dialysis fluid in the dialysis supply line (8).

In a 62nd independent aspect, an apparatus for extracorporeal blood treatment is provided comprising:

a filtration unit (2) having a primary chamber (3) and a secondary chamber (4) separated by a semi-permeable membrane (5);

a blood withdrawal line (6) connected to an inlet of the primary chamber (3), a blood return line (7) connected to an outlet of the primary chamber (3), said blood lines being configured for connection to a patient cardiovascular system;

a dialysis supply line (8);

a dialysis effluent line (13) connected to an outlet of the secondary chamber (4);

optionally a preparation device (9) for preparing a dialysis fluid connected to said supply line (8) and comprising regulating means (10) for regulating the composition of the dialysis fluid, a control unit (12), in particular connected to the regulating means (10), and programmed for receiving or calculating a value of a first parameter, said first parameter being at least one chosen in a group including a plasma conductivity, a plasma conductivity-related parameter, a concentration of the substance in the blood, a concentration-related parameter of the substance in the blood, a dialysis fluid concentration of a substance at a dialysis treatment in which the substance concentration of the dialysis fluid does not change pre- to post-filtration unit (2);

wherein said control unit (12) is configured for calculating a mass transport of a substance at an instant t of a treatment session based on said first parameter.

In a 63$^{rd}$ aspect according to the previous aspect, the control unit (12) is programmed for receiving a set value of a parameter for the dialysis fluid in the dialysis supply line (8), said parameter of the dialysis fluid being at least one chosen in a group including a conductivity of the dialysis fluid, a conductivity-related parameter of the dialysis fluid, a concentration of the substance in the dialysis fluid and a concentration-related parameter of the substance in the dialysis fluid;

wherein said control unit (12) is configured for calculating the mass transport of a substance at an instant t of the treatment session also based on said set value of the parameter for the dialysis fluid in the dialysis supply line (8).

In a 64$^{th}$ aspect according to anyone of the previous aspects 60 to 63, the control unit is configured to:

receive or calculate a value of a first parameter, the first parameter being chosen in the group including a plasma conductivity, a plasma conductivity-related parameter, a concentration of the substance in the blood, a concentration-related parameter of the substance in the blood, a dialysis fluid concentration of a substance at a dialysis treatment in which the substance concentration of the dialysis fluid does not change pre- to post-filtration unit (2); and calculate a mass transport of the substance at the instant t of the treatment session based on both said value of the first parameter and said set value of the parameter for the dialysis fluid in the dialysis supply line (8).

In a 65$^{th}$ aspect according to the previous aspect, the control unit is configured to calculate the mass transport of the substance as a function of a difference between the value of the first parameter and the set value of the parameter for the dialysis fluid in the dialysis supply line (8).

In a 66$^{th}$ aspect according to anyone of the previous aspects 64 or 65, the first parameter is a dialysis fluid concentration of sodium at an isonatric dialysis.

In a 67$^{th}$ aspect according to anyone of the previous aspects 60 to 66, the parameter for the dialysis fluid is a dialysis fluid concentration.

In a 68$^{th}$ aspect according to anyone of the previous aspects 60 to 67, the control unit is configured to calculate the mass transport of the substance as a function of a difference between a dialysis fluid concentration of sodium to provide isonatric dialysis and a dialysis fluid concentration set point.

In a 69$^{th}$ aspect according to anyone of the previous aspects 60 to 68, the control unit is configured to calculate the mass transport of the substance as a function of an efficiency parameter of the filtration unit (2) for the substance, in particular the clearance of the substance.

In a 70$^{th}$ aspect according to anyone of the previous aspects 60 to 69, the control unit is configured to calculate the mass transport of the substance as a function of a distribution volume of the substance.

In a 71$^{st}$ aspect according to anyone of the previous aspects 60 to 70, the control unit is configured to calculate a mass transport of the substance at the end of a treatment session as a function of a total treatment time.

In a 72$^{nd}$ aspect according to anyone of the previous aspects 60 to 71, the control unit is configured to calculate the mass transport of the substance as a function of a respective adjusting factor taking account of the Donnan effect.

In a 73$^{rd}$ aspect according to anyone of the previous aspects 60 to 72, the control unit is configured to calculate the mass transport of the substance as a function of an ultrafiltration flow rate.

In a 74$^{th}$ aspect according to anyone of the previous aspects 60 to 73, the control unit is configured to calculate the total mass transport or the diffusive mass transport or the convective mass transport.

In a 75$^{th}$ aspect according to anyone of the previous aspects 60 to 74, the control unit (12) is configured to calculate mass transfer as a function of one or more of the following:
- an efficiency parameter of the filtration unit (2) for the substance, in particular the clearance of the substance;
- a distribution volume of the substance;
- an ultrafiltration flow rate;
- an elapsed treatment time; and
- a respective adjusting factor taking account of the Donnan effect.

In a 76$^{th}$ aspect according to anyone of the previous aspects 60 to 75, the first parameter is the plasma conductivity and the parameter of the dialysis fluid is the concentration of the substance in the dialysis fluid, said substance being in particular sodium.

In a 77$^{th}$ aspect according to anyone of the previous aspects 60 to 76, the first parameter is a dialysis fluid concentration of sodium at an isonatric dialysis and the parameter of the dialysis fluid is the concentration of the substance in the dialysis fluid, said substance being in particular sodium.

In a 78$^{th}$ aspect according to anyone of the previous aspects 60 to 77, the control unit (12) is programmed for calculating the total mass transport value according to the following relationship:

$$M(t) = (Q_u \cdot c_{d,set} + \delta_d \cdot K_u) \cdot t + \frac{V_0}{\alpha} \cdot (\delta_0 - \delta_d) \cdot \left(1 - \left(1 - \frac{Q_u}{V_0} \cdot t\right)^{\frac{\alpha \cdot K_u}{Q_u}}\right) \quad \text{(XIV)}$$

wherein $$\delta_d = \frac{(1-\alpha) \cdot Q_u}{\alpha \cdot K_u - Q_u} \cdot c_{d,set} \quad \text{(XV)}$$

$$\delta_0 = c_{d,isoNa} - c_{d,set} \quad \text{(XVI)}$$

wherein:

| | |
|---|---|
| $M(t)$ | Total mass transport of sodium at instant t; |
| $c_{d,set}$ | Dialysis fluid sodium concentration set point; |
| $c_{d,isoNa}$ | Dialysis fluid concentration of sodium at an isonatric dialysis; |
| $Q_u$ | Ultrafiltration rate; |
| $V_0$ | Initial distribution volume of sodium; |
| t | Elapsed time of the treatment time; |
| $K_u$ | Filtration unit clearance for sodium; |
| $\alpha$ | Donnan factor; |

In a 79$^{th}$ aspect according to anyone of the previous aspects 60 to 77, the control unit (12) is programmed for calculating the diffusive mass transport value according to the following relationship:

$$M_d(t) = \left(Q_u \cdot \left(c_{d,set} - \frac{c_{d,isoNa}}{\alpha}\right) + \delta_d \cdot K_u\right) \cdot t + \frac{V_0}{\alpha} \cdot (\delta_0 - \delta_d) \cdot \left(1 - \left(1 - \frac{Q_u}{V_0} \cdot t\right)^{\frac{\alpha \cdot K_u}{Q_u}}\right) \quad \text{(XVII)}$$

wherein $$\delta_d = \frac{(1-\alpha) \cdot Q_u}{\alpha \cdot K_u - Q_u} \cdot c_{d,set} \quad \text{(XV)}$$

$$\delta_0 = c_{d,isoNa} - c_{d,set} \quad \text{(XVI)}$$

wherein:

| | |
|---|---|
| $M_d(t)$ | Diffusive mass transport of sodium at instant t; |
| $c_{d,set}$ | Dialysis fluid sodium concentration set point; |
| $c_{d,isoNa}$ | Dialysis fluid concentration of sodium at an isonatric dialysis; |
| $Q_u$ | Ultrafiltration rate; |
| $V_0$ | Initial distribution volume of sodium; |
| t | Elapsed time of the treatment time; |
| $K_u$ | Filtration unit clearance for sodium; |
| $\alpha$ | Donnan factor; |

In an 80$^{th}$ aspect according to anyone of the previous aspects 60 to 77, the control unit (12) is programmed for calculating the diffusive mass transport value according to the following relationship:

$$M_d(t) = (c_{d,set} - c_{d,isoNa}) \cdot \frac{V_0}{\alpha} \cdot \left(e^{\frac{\alpha \cdot K_u}{V} \cdot t} - 1\right) \quad \text{(XVIII)}$$

wherein:

| | |
|---|---|
| $M_d(t)$ | Mass transport of sodium at instant t; |
| $c_{d,set}$ | Dialysis fluid sodium concentration set point; |
| $c_{d,isoNa}$ | Dialysis fluid concentration of sodium at an isonatric dialysis; |
| $V_0$ | Initial distribution volume of sodium; |
| t | Elapsed time of the treatment time; |
| $K_u$ | Filtration unit clearance for sodium; |
| $\alpha$ | Donnan factor; |

In a 81$^{st}$ aspect according to anyone of the previous aspects 60 to 80, the control unit is configured to change the set value of the parameter for the dialysis fluid based on the calculated mass transport, in particular the control unit being configured to compare the calculated mass transport with a threshold and to change the set value based on the outcome of the comparison.

In a 82$^{nd}$ aspect according to anyone of the previous aspects 60 to 81, the control unit 12 is programmed according to any of aspects 35 to 59.

Further characteristics and advantages of the present invention will better emerge from the detailed description that follows of at least an embodiment of the invention, illustrated by way of non-limiting example in the accompanying figures of the drawings.

BRIEF DESCRIPTION OF THE DRAWINGS

The description will now follow, with reference to the appended FIGURE, provided by way of non-limiting example, in which:

FIG. 1 schematically represents an extracorporeal blood treatment apparatus made according to an illustrating embodiment.

DETAILED DESCRIPTION

Blood Treatment Apparatus

FIG. 1 illustrates an extracorporeal blood treatment apparatus 1 in an embodiment of the invention.

An example of a hydraulic circuit 100 is schematically illustrated, but it is to be noted that the specific structure of the hydraulic circuit 100 is not relevant for the purposes of the present invention and therefore other and different circuits to those specifically shown in FIG. 1 might be used in consequence of the functional and design needs of each single medical apparatus.

The hydraulic circuit 100 exhibits a dialysis fluid circuit 32 presenting at least one dialysis supply line 8. Depending on the specific apparatus treatment mode, the dialysis supply line 8 may or, may not, assume different hydraulic circuit line configurations.

In a hemodialysis (HD) treatment mode, the supply line 8 is destined to transport a dialysis fluid from at least one source 14 towards a treatment station 15 where one or more filtration units 2, or dialyzers, operate. Dialysis fluid and blood exchange through the semipermeable membrane in the filtration unit 15 mainly by diffusion process.

In a hemofiltration (HF) treatment mode, the supply line 8 comprises an infusion line 39, which is destined to transport an infusion fluid from at least one source 14 to the blood circuit. The infusion line 39 may include an ultrafilter 44 to additionally filter the received fluid upstream the injection point into the blood circuit. The removal of waste products from the blood is achieved by using large amounts of ultrafiltration with simultaneous reinfusion of sterile replacement fluid in the blood circuit.

In a hemodiafiltration (HDF) treatment mode, the supply line 8 is destined to transport the dialysis fluid from the source 14 towards the treatment station 15 and also comprises the infusion line 39 to transport the infusion fluid from the source 14 to the blood circuit 17. HDF is a combination of hemodialysis and hemofiltration.

In general, though not essential, the source 14 for the supply line 8 and the infusion line 39 is the same (i.e. a dialysis fluid preparation devices 9). Of course, different sources may be used.

Additionally, the supply line 8 normally branches into the infusion line 39, infusing fluid in the blood circuit 17, and into an inlet line 45 directing the fluid to the treatment station 15. Referring to FIG. 1, a branch point is indicated with reference numeral 46.

Notwithstanding the fact that different hydraulic circuits 100 may be used to deliver HF, HD and HDF treatments having exclusively the relevant lines for the specific treatment (e.g. no infusion line 39 for HD, no inlet line 45 for HF), generally the hydraulic circuit 100 is of the kind shown in FIG. 1 and includes both infusion line 39 and inlet line 45, the apparatus control unit 12 may then control the passage of fluid trough said lines, depending on the selected treatment, by means e.g. proper valves or clamps.

The dialysis fluid circuit 32 further comprises at least one dialysis effluent line 13, destined for the transport of a dialysate liquid (spent dialysate and liquid ultrafiltered from the blood through a semipermeable membrane 5) from the treatment station 15 towards an evacuation zone, schematically denoted by 16 in FIG. 1.

The hydraulic circuit cooperates with a blood circuit 17, also schematically represented in FIG. 1 in its basic component parts. The specific structure of the blood circuit is also not fundamental, with reference to the present invention. Thus, with reference to FIG. 1, a brief description of a possible embodiment of a blood circuit is made, which is however provided purely by way of non-limiting example.

The blood circuit 17 of FIG. 1 comprises a blood withdrawal line 6 designed to remove blood from a vascular access 18 and a blood return line 7 designed to return the treated blood to the vascular access 18.

The blood circuit 17 of FIG. 1 further comprises a primary chamber 3, or blood chamber, of the blood filtration unit 2, the secondary chamber 4 of which is connected to the hydraulic circuit 100.

In greater detail, the blood withdrawal line 6 is connected at the inlet of the primary chamber 3, while the blood return line 7 is connected at the outlet of the primary chamber 3.

In turn, the dialysis supply line 8 is connected at the inlet of the secondary chamber 4, while the dialysis effluent line 13 is connected at the outlet of the secondary chamber 4.

The filtration unit 2, for example a dialyzer or a plasma filter or a hemofilter or a hemodiafilter, comprises, as mentioned, the two chambers 3 and 4 which are separated by a semipermeable membrane 5, for example of the hollow-fibre type or plate type.

The blood circuit 17 may also comprise one or more air separators 19: in the example of FIG. 1 a separator 19 is included at the blood return line 7, upstream of a safety valve 20.

Of course other air separators may be present in the blood circuit, such as positioned along the blood withdrawal line 6.

The safety valve 20 may be activated to close the blood return line 7 when, for example, for security reasons the blood return to the vascular access 18 has to be halted.

The extracorporeal blood treatment apparatus 1 may also comprise one or more blood pumps 21, for example positive displacement pumps such as peristaltic pumps; in the example of FIG. 1, a blood pump 21 is included on the blood withdrawal line 6.

The apparatus of above-described embodiment may also comprise a user interface 22 (e.g. a graphic user interface or GUI) and a control unit 12, i.e. a programmed/programmable control unit, connected to the user interface.

The control unit 12 may, for example, comprise one or more digital microprocessor units or one or more analog units or other combinations of analog units and digital units. Relating by way of example to a microprocessor unit, once the unit has performed a special program (for example a program coming from outside or directly integrated on the microprocessor card), the unit is programmed, defining a plurality of functional blocks which constitute means each designed to perform respective operations as better described in the following description.

In combination with one or more of the above characteristics, the medical apparatus may also comprise a closing device operating, for example, in the blood circuit 17 and/or in the dialysis fluid circuit 32 and commandable between one first operating condition, in which the closing device allows a liquid to flow towards the filtration unit 2, and a second operative position, in which the closing device blocks the passage of liquid towards the filtration unit 2.

In this case, the control unit 12 may be connected to the closing device and programmed to drive the closing device to pass from the first to the second operative condition, should an alarm condition have been detected.

In FIG. 1 the closing device includes the safety valve 20 (e.g. a solenoid valve) controlled by the unit 12 as described above. Obviously a valve of another nature, either an occlusive pump or a further member configured to selectively prevent and enable fluid passage may be used.

Alternatively or additionally to the safety valve 20, the closing device may also comprise a bypass line 23 which connects the dialysis fluid supply line 8 and the dialysate effluent line 13 bypassing the dialyzer, and one or more fluid check members 24 connected to the control unit 12 for selectively opening and closing the bypass line 23. The components (bypass line 23 and fluid check members 24), which may be alternative or additional to the presence of the safety valve 20 are represented by a broken line in FIG. 1.

The check members 24 on command of the control unit close the fluid passage towards the treatment zone and connect the source 14 directly with the dialysis effluent line 13 through the bypass line 23.

Again with the aim of controlling the fluid passage towards the filtration unit 2, a dialysis fluid pump 25 and a dialysate pump 26 may be included, located respectively on the dialysis fluid supply line 8 and on the dialysate effluent line 13 and also operatively connected to the control unit 12.

The apparatus also comprises a dialysis fluid preparation device 9 which may be of any known type, for example including one or more concentrate sources 27, 28 and respective concentrate pumps 29, 30 for the delivery, as well as at least a conductivity sensor 35.

Of course other kinds of dialysis fluid preparation devices 9 might be equivalently used, having a single or further concentrate sources and/or a single or more pumps.

Since the dialysis apparatus may comprise various liquid sources 14 (for example one or more water sources, one or more concentrate sources 27, 28, one or more sources 33 of disinfectant liquids) connected to the dialysis supply line 8 with respective delivery lines 36, 37 and 38, the apparatus may exhibit, at each delivery line, a respective check member (not all are shown) and, for example, comprising a valve member 31 and 34 and/or an occlusive pump.

The preparation device 9 may be any known system configured for on-line preparing dialysis fluid from water and concentrates.

The dialysis supply line 8 fluidly connects the preparation device 9 for preparing dialysis fluid to the filtration unit 2 and/or to the blood circuit 17. The preparation device 9 may be, for example, the one described in the U.S. Pat. No. 6,123,847 the content of which is herein incorporated by reference.

As shown, the dialysis supply line 8 connects the preparation device 9 for preparing dialysis fluid to the filtration unit 2 and comprises a main line 40 whose upstream end is intended to be connected to a source 14 of running water.

Delivery line/s 36/37 is/are connected to this main line 40, the free end of which delivery line/s is/are intended to be in fluid communication (for example immersed) in a container/s 27, 28 for a concentrated saline solution each containing sodium chloride and/or calcium chloride and/or magnesium chloride and/or potassium chloride.

Concentrate pump/s 29, 30 is/are arranged in the delivery line/s 36/37 in order to allow the metered mixing of water and concentrated solution in the main line 40. The concentrate pump/s 29, 30 is/are driven on the basis of the comparison between 1) a target conductivity value for the mixture of liquids formed where the main line 40 joins the delivery line/s 36/37, and 2) the value of the conductivity of this mixture measured by means of a conductivity sensor 35 arranged in the main line 40 immediately downstream of the junction between the main line 40 and the delivery line/s 36/37.

Therefore, as mentioned, the dialysis fluid may contain, for example, ions of sodium, calcium, magnesium, and potassium and the preparation device 9 may be configured to prepare the dialysis fluid on the basis of a comparison between a target conductivity value and an actual conductivity value of the dialysis fluid measured by the conductivity sensor 35 of the device 9.

The preparation device 9 comprises regulating means 10, of a known type (i.e. concentrate pump/s 29, 30), which is configured to regulate the concentration of a specific substance, in particular an ionic substance, in the dialysis liquid. Generally it is advantageous to control the sodium concentration of the dialysis fluid.

The dialysis supply line 8 forms an extension of the main line 40 of the preparation device 9 for preparing dialysis fluid. Arranged in this dialysis supply line, in the direction in which the liquid circulates, there are the first flow meter 41 and the dialysis fluid pump 25.

The supply line 8 branches (at branch point 46) into the infusion line 39, which, in the example of FIG. 1, is shown directly connected to the blood return line 7, in particular to the air separator 19 (solid line) via post infusion tract 47*b*.

Alternatively, the infusion line 39 may infuse infusion fluid in the blood withdrawal line 6 via pre-infusion tract 47a, in particular downstream the blood pump 21 (dotted line) at pre-infusion point 48.

It is also in the scope of the present description an embodiment including an infusion line 39 branching into a pre-infusion branch 47a and in a post infusion branch 47b directing infusion fluid, respectively, in the blood withdrawal line 6 and in the blood return line 7.

One or more infusion pumps 43 may be used to pump the desired flow of infusion fluid into the blood circuit. The infusion pump 43 may be a positive displacement pump (e.g. a peristaltic pump as shown) or any other pump adapted to displace infusion fluid (e.g. a volumetric pump).

The dialysis effluent line 13 may be provided with a dialysate pump 26 and a second flow meter 42. The first and second flow meters 41, 42 may be used to control (in a known manner) the fluid balance of a patient connected to the blood circuit 17 during a dialysis session.

A sensor 11 is provided on the dialysis effluent line 13, immediately downstream the filtration unit 2, to measure a parameter value of the dialysate in the dialysate effluent line.

In detail, the parameter of the dialysate, which is measured by the sensor 11 is at least one chosen in the group consisting of conductivity of the dialysate, a conductivity-related parameter of the dialysate, concentration of at least a substance in the dialysate and a concentration-related parameter of at least a substance in the dialysate.

In detail the sensor 11 is a conductivity sensor, which is connected to the dialysis effluent line 13, and is configured to detect conductivity values of the dialysate downstream of the filtration unit 2.

Alternatively (or in combination) sensor 11 may include a concentration sensor configured for measuring the concentration of at least one substance in the dialysate, such as sodium concentration.

Correspondingly, sensor 35 on the dialysis fluid supply line may differently include a concentration sensor configured for measuring the concentration of at least one substance in the dialysis fluid, such as sodium concentration.

The control unit 12 of the dialysis apparatus represented in FIG. 1 may be connected to a (graphic) user interface 22 through which it may receive instructions, for example target values, such as blood flow rate $Q_b$, dialysis fluid flow rate $Q_{di}$, infusion liquid flow rate $Q_{inf}$ (pre infusion and/or post infusion), patient weight loss WL. The control unit 12 furthermore may receive detected values by the sensors of the apparatus, such as the aforementioned flow meters 41, 42, the (e.g. conductivity) sensor 35 of the preparation device 9 and the (e.g. conductivity) sensor 11 in the dialysis effluent line 13. On the basis of the instructions received and the operating modes and algorithms which have been programmed, the control unit 12 drives the actuators of the apparatus, such as the blood pump 21, the aforementioned dialysis fluid and dialysate pumps 25, 26, and the preparation device 9, and the infusion pump 43.

As already mentioned, the described embodiments are intended to be non-limiting examples. In particular the circuits of FIG. 1 should not be interpreted as defining or limiting, as an apparatus such as in the invention may comprise other additional or alternative components to those described.

For example an ultrafiltration line may be included, with at least one respective pump connected to the dialysis effluent line 13.

The blood circuit of FIG. 1 is intended for double needle treatments; however, this is a non-limiting example of the blood set.

Indeed, the apparatus may be configured to perform single needle treatments, i.e. the patient is connected to the extracorporeal blood circuit by way of a single needle and the extracorporeal line from the patient is then split into a withdrawal line and a return line, using, for example, an 'Y' connector. During single needle treatment, a blood withdrawal phase removing blood from patient is alternated to a blood return phase in which blood is restituted to the patient.

Furthermore one or more devices for measuring specific substance concentrations might be implemented either (or both) in the dialysis fluid side or (and) in the blood side of the hydraulic circuit. Concentration of calcium, potassium, magnesium, bicarbonate, and/or sodium might be desired to be known.

Finally, the above-cited one or more pumps and all the other necessary temperature, pressure, and concentration sensors may operate either on the dialysis supply line 8 and/or on the dialysis effluent line 13, in order to adequately monitor the preparation and movement of the liquid in the hydraulic circuit.

Given the above description of a possible embodiment of extracorporeal blood treatment apparatus, thereafter the specific working of the apparatus and the algorithm programming the control unit are described.

Definitions

We define the "dialysis fluid" as the fluid prepared and, when appropriate based on the selected treatment, introduced to the second chamber (4) of the filtration unit (2)—e.g. HD and HDF—. The dialysis fluid may also be denoted "fresh dialysis fluid".

We define the "dialysate" as the fluid from the outlet from the second chamber (4) of the filtration unit (2). Dialysate is the spent dialysis fluid, comprising the uremic toxins removed from the blood.

We define "infusion fluid" as the fluid prepared and infused in the blood circuit (17), either in the blood withdrawal line (6) or in the blood return line (7) or in both blood lines (6, 7).

We define "isonatric dialysis" as a treatment where the sodium concentration of the dialysis fluid does not change pre- to post-filtration unit 2. It is then assumed that the sodium concentration of the dialysis fluid matches the sodium concentration of the plasma, and thus the diffusive sodium mass transfer is zero.

We define "isotonic dialysis", as a treatment where the tonicity of the dialysis fluid does not change pre- to post-filtration unit 2. It is then assumed that the tonicity of the dialysis fluid matches the tonicity of the plasma.

We define "isoconductive dialysis", as a dialysis treatment where the conductivity of the dialysis fluid does not change pre- to post-filtration unit 2, $\kappa_{di}=\kappa_{do}$.

We define "plasma conductivity" (PC, $\kappa_p$) as the conductivity of the dialysis fluid in an isoconductive dialysis.

We define "mass transport", as the amount of a substance, usually given with the units grams or millimols, that is transported over the dialyzer membrane during a given time, usually the total treatment time.

We define "convective mass transport", as the amount of a substance in a thought volume where the volume is the total ultrafiltered volume (the patient volume loss and approximately mass loss) with a concentration identical to the matching blood concentration.

We define "diffusive mass transport", as the difference between total mass transport and convective mass transport.

In the present text, the term "desired mass transport" denotes the mass transport prescribed by the physician, taking in account the condition of the patient.

In this application the term "citrate" means that the component is in form of a salt of citric acid, such as sodium, magnesium, calcium, or potassium salt thereof. The citric acid (denoted $C_6H_8O_7$) is deprotonated stepwise, therefore the "citrate" include all the different forms, citrate (denoted $C_6H_5O_7^{3-}$), hydrogen citrate (denoted $C_6H_6O_7^{2-}$), and dihydrogen citrate (denoted $C_6H_7O_7^{-}$).

The term "citrate" or "total citrate" means that the total amount of citric acid and any salts thereof, such as its sodium, magnesium, calcium, or potassium salt thereof. In other terms, "total citrate" is the sum of free citrate ions and citrate containing complexes and ion pairs.

Glossary

The following terms are consistently used throughout the equations provided in the following description of the detailed working of the extracorporeal blood treatment apparatus.

| | |
|---|---|
| $c_{d,M_d}$ | Dialysis fluid sodium concentration to achieve a desired diffusive sodium mass transfer at the treatment time T; |
| $c_{d,M}$ | Dialysis fluid sodium concentration to achieve a desired total sodium mass transfer at the treatment time T; |
| $c_{d,isoNa}$ | Dialysis fluid concentration of sodium at an isonatric dialysis; |
| $c_{d,set}$ | Dialysis fluid concentration set point of sodium set by the operator; |
| $c_{d,isoNa,adj}$ | Sodium set point adjustment (relative to isoconductive state) required to provide isonatric dialysis; |
| $c_{d,Na,\kappa_{p,pre}}$ | Sodium concentration in the dialysis fluid to run an isoconductive dialysis; |
| $c_{d,Na,actual,i}$ | Actual dialysis fluid sodium concentration set point used during the treatment; |
| $c_{d,M_d,compensated}$ | Dialysis fluid sodium concentration new set point to compensate for unwanted substance transfer; |
| $\kappa_p$ | Plasma conductivity; |
| PC | |
| $\kappa_{p,1}$ | Plasma conductivity first estimate; |
| $\kappa_{p,2}$ | Plasma conductivity second estimate; |
| $\kappa_{p,pre}$ | Plasma conductivity at the beginning of the treatment; |
| $\kappa_{di}$ | Dialysis fluid conductivity at the filtration unit inlet; |
| $\kappa_{do}$ | Dialysis fluid conductivity at the filtration unit outlet; |
| $\kappa_{0,di}$ | Dialysis fluid conductivity at the filtration unit inlet for a pure electrolyte solution; |
| $\kappa_{0,do}$ | Dialysis fluid conductivity at the filtration unit outlet for a pure electrolyte solution; |
| $Q_b$ | Real blood flow rate; |
| $Q_u$ | Ultrafiltration rate; |
| $Q_{di}$ | Dialysis fluid flow rate (set); |
| $Q_{do}$ | Dialysate flow rate at the filtration unit outlet; |
| $Q_{bw}$ | Blood water flow rate; |
| $f_{bw}$ | Apparent blood water fraction for urea; |
| WL | Total weight loss; |
| $V_u$ | Expected total ultrafiltered volume; |
| M | Desired total mass transport of sodium (convective + diffusive); |
| $M_c$ | Desired convective mass transport of sodium; |
| $M_d$ | Desired diffusive mass transport of sodium; |
| $V_0$ | Total distribution volume (initial value); |
| $V_{Na^+}$ | Distribution volume of sodium; |
| $V_{HCO_3^-}$ | Distribution volume of bicarbonate; |
| $V_{Ac^-}$ | Distribution volume of acetate; |
| $V_{K^+}$ | Distribution volume of potassium; |
| $V_{rest,mean}$ | Mean distribution volume of the substances in the rest term; |
| T | Total treatment time (set); |
| t | Elapsed treatment time; |
| $K_u$ | Filtration unit clearance for urea; |
| $K_{b,Cit}$ | Filtration unit clearance for citrate; |
| $K_{u,Na^+}$ | Filtration unit clearance for sodium; |
| $K_{u,HCO_3^-}$ | Filtration unit clearance for bicarbonate; |
| $K_{Ac^-}$ | Filtration unit clearance for acetate; |
| $K_{u,K^+}$ | Filtration unit clearance for potassium; |
| $K_{u,rest,mean}$ | Mean clearance of the substances in the rest term; |
| $K_0A$ | Mass transfer coefficient of the filtration unit; |
| $M_{\kappa,NaHCO_3}$ | Molar conductivity of sodium bicarbonate ($NaHCO_3$) at ionic strength 150 mM; |
| $M_{\kappa,NaCl}$ | Molar conductivity of sodium chloride (NaCl) at ionic strength 150 mM; |
| $M_{\kappa,NaAc}$ | Molar conductivity of sodium acetate ($NaCH_3COO$) at ionic strength 150 mM; |
| $M_{\kappa,KCl}$ | Molar conductivity of potassium chloride (KCl) at ionic strength 150 mM; |
| $M_{\kappa,Na_3Cit}$ | Molar conductivity of trisodium citrate ($Na_3C_6H_5O_7$) at ionic strength 150 mM; |
| $\kappa_{rest3}$ | Conductivity contribution from lesser solutes 3; |
| $c_{pw,Na}$ | Estimated or measured pre-dialysis concentration of sodium ions ($Na^+$) in plasma water; |
| $c_{pw,HCO_3}$ | Estimated or measured pre-dialysis concentration of bicarbonate anions ($HCO_3^-$) in plasma water; |
| $c_{pw,Ac}$ | Estimated or measured pre-dialysis concentration of acetate anions ($CH_3COO^-$) in plasma water; |
| $c_{pw,K}$ | Estimated or measured pre-dialysis concentration of potassium ions ($K^+$) in plasma water; |
| $c_{pw,Na_3Cit}$ | Estimated or measured or known pre-dialysis concentration of total citrate in plasma water; |
| $c_{di,HCO_3}$ | Dialysis fluid concentration of bicarbonate as set by the operator; |
| $c_{di,Na}$ | Dialysis fluid concentration of sodium ions ($Na^+$) as set by the operator or by the control unit; |
| $c_{di,K}$ | Dialysis fluid concentration of potassium ions ($K^+$) as determined by the used concentrate; |
| $c_{di,Ac}$ | Dialysis fluid concentration of acetate as determined by the used concentrate; |
| $c_{di,Na_3Cit}$ | Dialysis fluid concentration of total citrate as determined by the used concentrate; |
| $\delta_{Na^+}(0)$ | Sodium driving gradient over filtration unit at instant t = 0; |
| $\delta_{HCO_3^-}(0)$ | Bicarbonate driving gradient over filtration unit at instant t = 0; |
| $\delta_{Ac^-}(0)$ | Acetate driving gradient over filtration unit at instant t = 0; |
| $\delta_{K^+}(0)$ | Potassium driving gradient over filtration unit at instant t = 0; |
| α | Donnan factor; |

The Donnan factor indicates a value of electroneutrality to be kept over the membrane. For estimating the Donnan factor reference is made to Trans Am Soc Artif Intern Organs, 1983; 29; 684-7, "Sodium Fluxes during hemodialysis", Lauer A., Belledonne M., Saccaggi A., Glabman S., Bosch J.

Solution Proposal

The technical solution here described consists of three main parts:
Estimating/calculating or receiving either PC (i.e., $\kappa_p$, $\kappa_{p,pre}$) or dialysis fluid concentration of sodium to provide isonatric dialysis (i.e. $c_{d,isoNa}$) at the beginning of the treatment;
Setting the dialysis fluid sodium concentration such that a desired mass transport (M; $M_d$) is achieved at the end of the treatment session;
Maintaining the dialysis fluid composition throughout the treatment.

The various steps of the proposed method described below are intended to be performed by the control unit 12 of the extracorporeal blood treatment device 1, even if not explicitly stated.

In particular a treatment session is started, preferably, but not necessarily, as a double needle hemodialysis treatment.

The user shall input the prescription values through the user interface 22. For example the set values for total weight loss WL and total treatment time T are provided, as well as the blood flow rate $Q_b$ and the fresh dialysis flow rate $Q_{di}$.

The user may input either the desired total (diffusive+convective) sodium mass transport M or the desired sodium diffusive mass transport $M_d$ over the treatment. Alternatively, desired mass transport might also be denoted personalized, or individualized, mass transport.

Other parameters may be entered through the user interface, such as bag type, sodium user limits, etc.

The operator has to further input the 'bicarbonate' set before starting the treatment.

The First Parameter Value (e.g. Plasma Conductivity or $c_{d,isoNa}$)

According the above discussed approach, the control unit 12 receives either a dialysis fluid concentration of sodium to provide isonatric dialysis (i.e. $c_{d,isoNa}$) or a value representative of a parameter of the blood in said blood lines 6, 7. The blood related parameter may be concentration of a substance in the blood plasma (e.g. sodium), a concentration-related parameter of said substance in the blood, the plasma conductivity or a plasma conductivity-related parameter.

In a first embodiment, the control unit 12 receives the dialysis fluid concentration of sodium to provide isonatric dialysis (i.e. $c_{d,isoNa}$). This value may be know from previous calculations or estimated e.g. based on previous treatments on the same patient. In case the apparatus directly receives or determines the above sodium concentration, the control unit is configured to apply the procedure described in the following paragraph named "Adjustment term to achieve the desired sodium balance".

In another embodiment, the control unit 12 directly receives as an input the plasma conductivity or the plasma sodium concentration. For example, the physician or the nurse may receive a lab analysis and may provide the datum to the machine through the user interface of the dialysis monitor; the control unit 12 is programmed for storing in a memory the plasma conductivity/plasma sodium concentration to be used for the following dialysis fluid parameter regulation.

The plasma conductivity (or sodium concentration) may be directly measured in vivo by the monitor before starting the treatment session using a proper plasma conductivity/concentration sensor. In case the apparatus directly receives the above plasma conductivity/plasma sodium concentration, the control unit is configured to apply the procedure described in the following paragraph named "Determining isonatric dialysis set point".

Alternatively, the control unit 12 may be programmed for calculating the plasma conductivity, for example using known methods such as those described in EP 2377563.

In an additional embodiment which here in after briefly presented and disclosed, the plasma conductivity may be calculated by the machine according to the following procedure which starts with a proper initial set of the dialysis fluid and determines the plasma conductivity with a specific algorithm.

The control unit 12 is generally configured for setting a parameter value for the dialysis fluid in the dialysis supply line 8 at an initial set point.

The parameter of the dialysis fluid is chosen between a conductivity of the dialysis fluid, a conductivity-related parameter of the dialysis fluid, a concentration of a substance in the dialysis fluid and a concentration-related parameter of a substance in the dialysis fluid.

Depending on the specific dialysis monitor, the sodium content (or the content of more than one electrolyte) may be regulated in the dialysis line. Alternatively, the control parameter may be the overall conductivity of the dialysis fluid.

The setting of the parameter value in the dialysis fluid (which is hereinafter identified as sodium concentration set point in the dialysis fluid with no limiting effect) includes the sub-step of calculating the sodium concentration initial set point.

The control unit 12 calculates either the initial dialysis liquid conductivity or the initial concentration of at least one solute, e.g. sodium, in the dialysis liquid in order to start with a dialysis fluid conductivity as close as possible to the expected patient pre-dialytic plasma conductivity.

In order to not disturb the tonicity of the patient, it is necessary to set the fluid composition as quickly as possible so that the patient initial plasma conductivity is not inadvertently changed. Thus, estimating of the plasma conductivity has to be done as rapidly as possible when treatment starts; moreover, since the estimation is preferably performed only once, this measure should be as reliable as possible.

Reference is made to regulating means controlling concentration of an ionic substance, in detail sodium concentration, in the preparation of the dialysis fluid so as to obtain a desired conductivity of the dialysis fluid.

However, regulating means directly regulating the overall dialysis fluid conductivity is also included in the spirit of the present description or, alternatively, regulating means modifying the concentration of a different ionic substance is included in the present description, too.

In detail, the control unit 12 is configured to set the parameter value for the dialysis fluid at the initial set point so that a dialysis fluid conductivity matches a first estimate of the plasma conductivity of the blood.

In the specific, the control unit 12 calculates the initial set point of the substance concentration and drives the regulating means 10 acting on the sodium concentration in the dialysis liquid.

The set point is calculated before starting the blood circulation (i.e. before starting the treatment).

In order to calculate the dialysis composition initial set point alternative ways might be used, e.g. determine a certain sodium concentration (see below), or using an average plasma conductivity from a large population, or using an average plasma conductivity from a large population corrected for the composition of the dialysis fluid, or calculate based on historic patient data.

In any case, the initial set point for the dialysis liquid is calculated by the control unit 12 so that the expected plasma conductivity is the best guess of plasma conductivity that may be calculated, without prior knowledge of the individual patient.

Once the sodium initial set point has been calculated and a corresponding dialysis fluid has been prepared by the control unit 12 driving the regulating means 10, the treatment may start.

The dialysis fluid is circulated through the dialysis fluid circuit 32 so as to exchange with and/or to be infused into blood.

Correspondingly, blood is withdrawn from the patient and circulated in the extracorporeal blood circuit 17 and particularly is circulated through the primary chamber 3 of the filtration unit 2.

At least one, and in general a plurality, of consecutive initial values of the parameter (in the specific example, the conductivity) of the dialysate downstream of the secondary chamber 4 are measured at the beginning of the treatment through sensor 11. The control unit 12 is configured to validate and further process the measurement of an initial value of the conductivity of the dialysate as soon as the diffusion process in the filtration unit 2 reaches stable conditions. Indeed, a transient exists when dialysis fluid and blood start exchanging during which the dialyzer outlet conductivity is not stable; during the transient period the measured outlet conductivity values should be disregarded.

Glucose and urea, the main electrically neutral substances in dialysis fluid, reduce the conductivity of the dialysis fluid. Hence, a compensation for urea and glucose contribution may also be applied to the measured conductivities $\kappa_{di}$ and $\kappa_{do}$: the resulting conductivities for pure ion solutions ($\kappa_{0,di}$ and $\kappa_{0,do}$) may alternatively be used in all the calculations using conductivities reported below.

It is worth to note that the initial conductivity of the fresh dialysis fluid upstream the secondary chamber 4, namely $\kappa_{di}$, may be either measured or taken as the set value for dialysis conductivity.

In general, it is preferred to measure the initial conductivity of the dialysis fluid through the sensor 35, too.

The initial setting of the sodium concentration calculated or determined as above stated to be as close as possible to the expected plasma conductivity may be optional, meaning that the method for estimating the initial plasma conductivity may be performed even if the sodium content of the dialysis conductivity is initially simply set by the operator. Also correction based on main electrically neutral substances is optional and may be used or not to increase accuracy.

Vice versa, it is relevant to measure at least the conductivity downstream the filtration unit (and preferably also the conductivity upstream the filtration unit) as soon as possible, i.e. as soon as stable conditions are reached or as soon as an estimate of such conductivity in stable conditions may be performed.

In order to make a first estimate of the plasma conductivity based on measured values, firstly, the control unit 12 calculates the value of the initial plasma conductivity, based on the measured initial parameter value of the dialysate (i.e. based on conductivity or concentration measurement of dialysate on the filtration unit outlet) and on the corresponding parameter value of the dialysis fluid in the dialysis fluid supply line 8 e.g. conductivity or concentration). During the start of the treatment and particularly during circulating the dialysis fluid through the secondary chamber 4 up to measuring the initial value of the parameter of the dialysate downstream of the secondary chamber used for the calculating of the initial plasma conductivity, the dialysis fluid conductivity (or concentration) is kept substantially constant.

In this respect the term 'substantially constant' means that the conductivity of the dialysis fluid is not changed by the machine or by the operator, but it may not be exactly constant due to small oscillations on the measured value caused by noise, tolerances in the concentrate dosing system or tolerances in the conductivity measurements. Generally these small variations around the set value are less than 0.2 mS/cm.

Just a single reliable measurement at the inlet and at the outlet of the dialyzer may be sufficient to have a preliminary (to be made more accurate) or an already final estimation of the PC.

From a general point of view, the control unit 12 is configured to calculate the plasma conductivity as a function of at least one or more of the following parameters:

one flow rate, namely the dialysate flow rate at the outlet of the secondary chamber 4;

an efficiency parameter of the filtration unit 2, in particular a clearance of the filtration unit 2 (e.g. the urea clearance). Of course, a nominal clearance and/or a calculated clearance may be used and the calculated clearance may be both an estimated clearance as well as a compensated clearance;

an (possibly compensated) initial conductivity of the dialysate and a (possibly compensated) conductivity of the dialysis fluid in the dialysis supply line 8.

In more detail, the control unit 12 is programmed to calculate the initial plasma conductivity based on the sum of at least the initial conductivity of the fresh dialysis fluid plus a difference between inlet and outlet conductivity at the dialyzer weighted by a factor of the dialysate flow rate. The difference between inlet and outlet conductivity at the filtration unit, or dialyzer, is weighted by a factor of the dialyzer clearance too.

Specifically, the control unit 12 is configured to calculate the plasma conductivity using the following formula:

$$\kappa_{p,1} = \kappa_{0,di} + \frac{Q_{do}}{K_u}(\kappa_{0,do} - \kappa_{0,di}) \tag{1}$$

The significance of the denotations and constants above is given in the Glossary.

It is worth to underline that during the above described calculation of the initial plasma conductivity (formula (1)), the dialysis fluid circulates through the secondary chamber 4 maintaining the dialysis fluid parameter value substantially constant.

In more detail, in the formulas above:

$k_{0,di}$ is the set/measured-by-sensor 35 value for conductivity of the dialysis fluid, optionally corrected for glucose;

$k_{0,do}$ is the mean value of outlet conductivity in stable conditions, corrected for glucose and urea;

$Q_{di}$ is the set value for dialysis fluid flow rate;

$Q_{do}$ is the mean value of dialysate flow rate at the filtration unit, or dialyzer, outlet, in stable conditions;

$K_u$ is the dialyzer diffusive clearance for urea. Since $K_u$ may not be known, different estimates may be used.

$K_u$ may be approximated as $Q_{di}/2$.

Alternatively, $K_u$ may be calculated as follows:

$$K_u = Q_{bw} Q_{di} \frac{1 - e^{KoA\left(\frac{1}{Q_{di}} - \frac{1}{Q_{bw}}\right)}}{Q_{di} - Q_{bw} e^{KoA\left(\frac{1}{Q_{di}} - \frac{1}{Q_{bw}}\right)}} \tag{2}$$

where

KoA is either a known value if the control unit has information about the dialyzer used. In case the control unit has no information on the used dialyzer, a standard dialyzer value with a KoA=1100 ml/min as a fixed value may be used.

$Q_{bw}$ is the blood water flow, for example, calculated as:

$$Q_{bw}=f_{bw} \cdot Q_b = 0.89 \cdot Q_b \tag{3}$$

where $Q_b$ is real blood flow rate and $f_{bw}$ is the apparent blood water fraction for urea, where a hematocrit of 30% has been assumed.

Of course, formula (1) for estimation of plasma conductivity may be iteratively applied, meaning that the newly calculated estimate of PC ($k_{p,1}$) is imposed to the dialysis fluid and a new estimate again calculated after taking measures of the conductivity at the inlet and outlet of the filter as soon as stable conditions are reached.

Of course, in case of iteration, after the first plasma conductivity estimation, the dialysis fluid parameter value is changed since the newly calculated estimate of PC ($k_{p,1}$) is imposed to the dialysis fluid, meaning that the conductivity of the dialysis fluid is changed. This however does not impact on the fact that the first calculation according to formula (1) is made without a change in the conductivity of the dialysis fluid.

The dialysis fluid sodium concentration correspondent to $k_{p,pre}$ is then determined. The resulting dialysis fluid sodium concentration applied, $c_{d,Na,kp,pre}$, would correspond to implement an isoconductive dialysis.

Determining Isonatric Dialysis Set Point

Since a sodium set value for an isonatric dialysis is to be determined, the sodium concentration, $c_{d,Na,kp,pre}$, (corresponding to implement an isoconductive dialysis) is to be adjusted with a proper adjustment factor.

The adjustment contribution term is the sodium concentration set point adjustment relative to an isoconductive state to provide an isonatric dialysis.

In order to obtain a dialysis fluid sodium implementing isonatric dialysis, i.e. $c_{d,isoNa}$, an adjustment factor $c_{d,isoNa,adj}$ needs to be applied to make the sodium concentration of dialysate out from the dialyzer matching the sodium concentration of dialysis fluid at the inlet of the dialyzer:

$$c_{d,isoNa} = c_{d,Na,kp,pre} + c_{d,isoNa,adj} \tag{4}$$

In case of an isonatric treatment is to be performed, the mentioned adjustment factor may be calculated based on molar conductivities, dialysis fluid composition and the best estimate of plasma water composition.

In particular:

$$c_{d,isoNa,adj} = -\frac{1}{M_{k_{NaCl}}}\left( (M_{k_{NaHCO_3}} - M_{k_{NaCl}})\left(\frac{1}{\alpha} * c_{pw,HCO_3} - c_{di,HCO_3}\right) + \right. \tag{5}$$
$$(M_{k_{NaAc}} - M_{k_{NaCl}})\left(\frac{1}{\alpha} * c_{pw,Ac} - c_{di,Ac}\right) +$$
$$\frac{K_{b_{Cit}}}{K_u}(M_{k_{Na_3Cit}} - 3M_{k_{NaCl}})((0.167\alpha^{-3} + 0.125\alpha^{-2} + 0.706\alpha^{-1}) *$$
$$\left. c_{pw,Na_3Cit} - c_{di,Na_3Cit}) + M_{k_{KCl}}(\alpha * c_{pw,K} - c_{di,K}) + \frac{Q_{do}}{K_u}\kappa_{rest3}\right)$$

$K_{b_{Cit}}$ is the approximated clearance value for citrate. This clearance is calculated for the actual flow rates using a mass transfer value of $K_0 A_{Cit} = 0.212 * K_0 A_{Urea}$ in the corresponding $K_u$ formula.

Factor k (namely, $k_{rest3}$) defines the effect on the conductivity due to other components in the dialysis fluid different from the components already treated and included in the respective formula. Thus, the effect of salts containing calcium, magnesium, lactate, phosphate, and sulphate may have upon the conductivity. The effect created by these components is most often small, and does not vary considerably between the dialysis treatments.

Adjustment Term to Achieve the Desired Sodium Balance

Once the sodium set point for running an isonatric treatment is determined (e.g. calculated or received), the control unit 12 is configured to adapt the dialysis fluid set point in order to match a desired mass transport at the end of the treatment session. In particular, the following embodiments refer to sodium; in other term, the sodium set point is calculated in order to match the desired total sodium mass transport M (diffusive+convective–M=$M_d$+$M_c$) or the desired diffusive sodium mass transport $M_d$.

However, the following equations for the quantification of sodium balance may be used for other substances that are distributed in one distribution volume.

The equation system may work with e.g. urea, bicarbonate and chloride. An issue may be to determine the 'isoX' value for substance X corresponding to 'isoNa' value for sodium. Urea cannot be determined by a conductivity method; however, a measured value of the plasma concentration could be used. Of course, the corresponding parameters for the other substance (e.g. urea) should be entered into the here-below detailed equations.

If the sodium set point for running an isonatric treatment is applied at the beginning of the treatment session, a zero diffusive mass transport of sodium is obtained. Therefore, the physician, who requires a net mass transport, shall input either the desired total mass transport M of sodium or the desired diffusive mass transport $M_d$ of sodium, e.g. with the prescription, and the apparatus calculates the adjustment contribution term to be imposed to adjust the previously determined sodium set point. The updated set point is determined so that the desired mass transport M; $M_d$ of sodium is achieved at the end of the treatment session, i.e. at the end of the total treatment time T.

Clearly, the setting of the second parameter value (conductivity/concentration of sodium) in the dialysis fluid is a function of the desired mass transport received as an input.

In more detail, the control unit 12 is configured to calculate the second parameter value (i.e. sodium concentration for the dialysis fluid) as a function of a main contribution term and as a function of an adjustment contribution term based on the desired mass transport (being it the total mass transport M or the diffusive mass transport $M_d$). In particular, the sodium concentration for the dialysis fluid is calculated as a sum of the main contribution term and of the adjustment contribution term. The main contribution term is a dialysis fluid concentration of sodium at an isonatric dialysis ($c_{d,isoNa}$); the adjustment contribution term is the sodium concentration set point adjustment relative to an isonatric dialysis to provide a treatment configured to achieve the desired total or diffusive mass transport over the treatment time.

The control unit is programmed to calculate the adjustment contribution term as a function of one or more (and in particular all) of the following parameters:

an efficiency parameter of the filtration unit 2 for the substance, in particular the clearance of the filtration unit for the substance;

a distribution volume of the substance;
the ultrafiltration rate and/or the total ultrafiltered volume;
a treatment time, in particular the total treatment time; and
a respective adjusting factor which takes into account the Donnan effect.

The second parameter value, which is here a concentration, may be determined taking into account the ultrafiltration or disregarding the ultrafiltration.

In case ultrafiltration is disregarded, the second parameter value may be calculated according to the following formula:

$$c_{d,M_d} = c_{d,isoNa} + \frac{\alpha \cdot M_d}{V \cdot \left(e^{\frac{\alpha \cdot K_b}{V} \cdot T} - 1\right)} \quad (6A)$$

wherein the used symbols meaning is clarified in the glossary section.

Notably, the ultrafiltration causes a volume loss in the patient during the treatment, thereby changing the considered concentrations. In a more precise determination of the dialysis fluid concentration to achieve the desired mass transport, ultrafiltration rate and its effects are considered.

In this latter case, the second parameter value may be determined in accordance with the following mathematical relationships:

to achieve a desired total mass transport: eq. 6B—

$$c_{d,M} = c_{d,isoNa} + \frac{M - (V_2 - f_{cd} \cdot V_1) \cdot c_{d,isoNa}}{V_2 - (1 + f_{cd}) \cdot V_1} \quad (6B)$$

to achieve a desired diffusive mass transport: eq. 6C—

$$c_{d,M_d} = c_{d,isoNa} + \frac{M_d - \left(V_2 - f_{cd} \cdot V_1 - \frac{V_u}{\alpha}\right) \cdot c_{d,isoNa}}{V_2 - (1 + f_{cd}) \cdot V_1} \quad (6C)$$

wherein $f_{cd}$, $V_1$, $V_2$ and $V_u$ are:

$$f_{cd} = \frac{(1-\alpha) \cdot Q_u}{\alpha \cdot K_u - Q_u} \quad (7)$$

$$V_1 = \frac{V_0}{\alpha} \cdot \left(1 - \left(1 - \frac{V_u}{V_0}\right)^{\frac{\alpha \cdot K_u}{Q_u}}\right) \quad (8)$$

$$V_2 = f_{cd} \cdot K_u \cdot T \cdot V_u \quad (8)$$

$$V_u = Q_u \cdot T \quad (10)$$

and wherein the used symbols meaning is clarified in the glossary section.

As mentioned, the second term is the adjustment contribution term which added to the dialysis fluid concentration of sodium at an isonatric dialysis allows to achieve the wanted sodium balance.

With these formulas the dialysis fluid sodium concentration can be set to get a predetermined sodium mass balance over the treatment based on estimations of parameters that are fairly good known as the initial sodium distribution volume ($V_0$—total body water), clearance ($K_u$), duration of treatment (T), the ultrafiltration flow rate ($Q_u$) and the Donnan factor ($\alpha$).

Once the set point for sodium $c_{d,M}$; $c_{d,M_d}$ is calculated, the control unit 12 drives the regulating means 10 for regulating the conductivity or the concentration of the substance in the fresh dialysis fluid and sets the parameter value for the dialysis fluid in the dialysis fluid supply line 8 at the calculated set point.

Determination of the Sodium Mass Transport

There are two fundamental ways to evaluate the physiological effects of substance transport from or to the patient during a dialysis treatment. The first way is the idea of an ideal plasma concentration of a substance that represents a homeostatic state. To achieve that plasma concentration a corresponding dialysis fluid setting is selected and the dialysis process drives the plasma concentration towards the desired concentration. The second way to quantify the effect is to study the mass balance or dose the treatment causes. This will in the long run match the net intake by food for the substance. Regarding sodium it is more beneficial to know the mass balance than its concentration as it is the total mass of sodium that distributes water between extracellular and intracellular space. A homeostatic volume of the extracellular space is crucial for heart function and blood pressure control.

In the spirit of the present description, the apparatus for extracorporeal blood treatment may also be configured to determine the (total or diffusive) mass transport of the substance (e.g. sodium).

The mass transport is the amount of a substance, usually given with the units grams or millimols, that is transported over the dialyzer membrane during a given time (usually the total treatment time). If the mass transport are from the blood to the dialysis fluid and thus leaving the patient it is by convention given a positive sign. If the mass transport is from the dialysis fluid to the blood it is given a negative sign. Other names used in the literature are mass transfer and mass balance. For a momentary effect the common term is mass transfer rate.

Further, mass transport can be divided in two parts, the convective part and the diffusive part. The convective part is the mass in a thought volume where the volume is the total ultrafiltered volume (the patient volume loss and approximately mass loss) with a concentration identical to the matching blood concentration. A dialysis with a total mass transport identical to convective mass transport will not change the concentration in blood. The diffusive mass transport is the difference between total mass transport and convective mass transport.

Based on the knowledge of the patient, regarding food and intake of salt, a desired mass transport can be prescribed. If the patient has a history of hypotensive episodes one may prescribe a certain amount of sodium to be added during the treatment. If the patient has a tendency to hypertension an amount of sodium may be removed. These prescriptions can be calculated on total mass transport or diffusive mass transport.

In this respect the physician may set a desired target of plasma conductivity to be reached at the end of the treatment (e.g. by properly setting the dialysis fluid conductivity) and the apparatus perform the extracorporeal blood treatment so as to change the plasma conductivity of the patient towards the target.

During the course of the treatment, the control unit may monitor and display the substance mass transport achieved at the treatment time t. Anyone or all of the diffusive, convective or total mass transport may be monitored.

Knowing the total sodium balance (or the diffusive sodium balance or the convective sodium balance) at a certain treatment time t may help the physician to adapt the treatment to the patient by e.g. modifying treatment parameters (for example the dialysis fluid conductivity) during the treatment itself; in any case a relevant information is provided in terms of total sodium transport.

To calculate the achieved mass transport, the control unit 12 receives/calculates the dialysis fluid sodium concentration set point, $c_{d,set}$; the operator may indeed input such concentration or the dialysis fluid conductivity set point at the start of the treatment.

Moreover, the control unit 12 should receive as input or determine as above described, the dialysis fluid concentration of sodium to provide isonatric dialysis, i.e. $c_{d,isoNa}$.

The mass transport achieved at instant t of the extracorporeal blood treatment ($M(t)$; $M_d(t)$; $M_c(t)$) is function of at least:
- the dialysis fluid concentration of sodium to provide isonatric dialysis, i.e. $c_{d,isoNa}$;
- the ultrafiltration flow rate $Q_u$;
- the elapsed treatment time t; and
- the Donnan factor $\alpha$.

In case the convective mass transport is of interest, the same may be calculated as follows:

$$M_c(t) = Q_u \cdot \frac{c_{d,isoNa}}{\alpha} \cdot t \tag{11}$$

wherein the used symbols meaning is clarified in the glossary section.

The total mass transport and the diffusive mass transport achieved at instant t of the extracorporeal blood treatment are both function of the above listed parameters and of the dialysis fluid sodium concentration set point, $c_{d,set}$, and in more detail of the difference in concentration between the dialysis fluid sodium concentration set point and the dialysis fluid concentration of sodium to provide isonatric dialysis, i.e. $\delta_0 = c_{d,isoNa} - c_{d,set}$. Furthermore, the achieved total mass transport and the diffusive mass transport are a function of the efficiency parameter $K_u$ of the filtration unit 2 for the substance, in particular the clearance of the substance, the elapsed treatment time t, the Donnan factor $\alpha$ and the initial distribution volume $V_0$.

The total mass transport is the sum of two different terms, a first term based on the ultrafiltration flow rate, the efficiency parameter of the filtration unit, the elapsed time, the Donnan factor and the set conductivity in the dialysis fluid. The second term being function of the distribution volume, the Donnan factor, the efficiency parameter of the filtration unit, the elapsed time, the ultrafiltration flow rate, as well as the dialysis fluid concentration of sodium to provide isonatric dialysis.

The specific mathematical relation to be used for determination of the total mass transport is the following:

$$M(t) = (Q_u \cdot c_{d,set} + \delta_d \cdot K_u) \cdot t + \frac{V_0}{\alpha} \cdot (\delta_0 - \delta_d) \cdot \left(1 - \left(1 - \frac{Q_u}{V_0} \cdot t\right)^{\frac{\alpha \cdot K_u}{Q_u}}\right) \tag{12}$$

$$\delta_d = \frac{(1-\alpha) \cdot Q_u}{\alpha \cdot K_u - Q_u} \cdot c_{d,set} \tag{13}$$

$$\delta_0 = c_{d,isoNa} - c_{d,set} \tag{14}$$

wherein the used symbols meaning is clarified in the glossary section.

If the diffusive mass transport is to be determined, the difference between total and convective mass transport may be used.

The equation for deriving the diffusive mass transport is the following:

$$M_d(t) = \left(Q_u \cdot \left(c_{d,set} - \frac{c_{d,isoNa}}{\alpha}\right) + \delta_d \cdot K_u\right) \cdot t + \frac{V_0}{\alpha} \cdot (\delta_0 - \delta_d) \cdot \left(1 - \left(1 - \frac{Q_u}{V_0} \cdot t\right)^{\frac{\alpha \cdot K_u}{Q_u}}\right) \tag{15}$$

With the aid of the above formulas, the physician may determine the sodium mass transfer (total, convective and diffusive) at any time t during the treatment. Of course, substituting t with the total treatment time T, the operator may know the total diffusive mass transport of sodium of the entire treatment.

The control unit 12 may also be configured to change a prescription value e.g. the sodium set point for the dialysis fluid based on the determined mass transport so that, in case of abnormal or undesired transport, the remaining part of the treatment may compensate the sodium transport.

Online Validation of Electrolyte Transport

In case the apparatus is configured to achieve a set mass transport, once the treatment session is started using the calculated set point for the dialysis fluid, e.g. $c_{d,M}$; $c_{d,M_d}$, the conductivity of the dialysate post the filtration unit 2 can be measured and analyzed. The individual values of $K_u$ for the substances are used. The dialysis fluid concentration of the different substances are assumed fixed and the plasma water concentrations may alternatively be modeled individually, using the best available models known from literature.

During the treatment at any time t, the modeled $\kappa_{do}(t)$ may be calculated according to the formula here below reported:

$$\kappa_{do}(t) = \kappa_{di} + \frac{K_{u,Na^+}}{Q_{do}} \cdot M_{\kappa_{NaCl}} \cdot \tag{16}$$

$$\left(\delta_{d,Na^+} + (\delta_{0,Na^+} - \delta_{d,Na^+}) \cdot \left(1 - \frac{Q_u}{V_{0,Na^+}} \cdot t\right)^{\frac{\alpha \cdot K_{u,Na^+}}{Q_u} - 1}\right) +$$

$$\frac{K_{u,HCO_3^-}}{Q_{do}} \cdot (M_{\kappa_{NaHCO_3}} - M_{\kappa_{NaCl}}) \cdot$$

$$\left(\delta_{d,HCO_3^-} + (\delta_{0,HCO_3^-} - \delta_{d,HCO_3^-}) \cdot \left(1 - \frac{Q_u}{V_{0,HCO_3^-}} \cdot t\right)^{\frac{\alpha^{-1} \cdot K_{u,HCO_3^-}}{Q_u} - 1}\right) +$$

$$\frac{K_{u,Ac^-}}{Q_{do}} \cdot (M_{\kappa_{NaAc}} - M_{\kappa_{NaCl}}) \cdot$$

$$\left(\delta_{d,Ac^-} + (\delta_{0,Ac^-} - \delta_{d,Ac^-}) \cdot \left(1 - \frac{Q_u}{V_{0,Ac^-}} \cdot t\right)^{\frac{\alpha^{-1} \cdot K_{u,Ac^-} + \frac{V_{max}}{K_M}}{Q_u} - 1}\right) +$$

$$\frac{K_{u,K^+}}{Q_{do}} \cdot M_{\kappa_{KCl}} \cdot \left(\delta_{d,K^+} + (\delta_{0,K^+} - \delta_{d,K^+}) \cdot \left(1 - \frac{Q_u}{V_{0,K^+}} \cdot t\right)^{\frac{\alpha \cdot K_{u,K^+}}{Q_u} - 1}\right) +$$

$$K_{rest3} \cdot e^{\frac{K_{u,rest,mean}}{V_{rest,mean}} \cdot t}$$

wherein the time variable gradients are denoted:

$$\delta_{d,Na^+} = \alpha \cdot c_{pw,Na}(t) - c_{di,Na}$$

$$\delta_{d,HCO_3^-} = \frac{1}{\alpha} \cdot c_{pw,HCO_3}(t) - c_{di,HCO_3}$$

-continued $$\delta_{d,Ac^-} = \frac{1}{\alpha} \cdot c_{pw,Ac}(t) - c_{di,Ac}$$

$$\delta_{d,K^+} = \alpha \cdot c_{pw,K}(t) - c_{di,K}$$

and wherein the other used symbols meaning is clarified in the glossary section.

The modeled conductivity is then compared with the measured conductivity to check that the dialysis progresses as expected with the used estimations of sodium, bicarbonate and potassium.

Compensation for Unwanted Sodium Transfer

After the application of sodium adjustments above described, the inlet conductivity correspondent to the fresh dialysis fluid sodium concentration determined with Eq. 6 shall then be kept constant throughout the remainder of the treatment.

After the setting of the sodium set point for achieving the desired mass transfer, the plasma conductivity may be further calculated/monitored using common procedures, such as those described in patents EP 547025 or in EP 920877 to monitor PC throughout the treatment.

During the identification phase (i.e. plasma conductivity initial estimate), the sodium setting is likely to be too high, leading to unwanted sodium load. The time for this estimation may slightly vary, but as an average is about 15 minutes; accordingly, the magnitude of the error is in the range of 5 mmol/l (of course varying with how well the expected plasma conductivity matches the actual plasma conductivity, as well as the magnitude of the isotonic adjustment).

To maintain the patient's sodium balance during the dialysis treatment, the calculated sodium set value must be adjusted to compensate for any additional unwanted sodium load to the patient.

Moreover, if common procedures such as those described in patents EP 547025 or in EP 920877 to monitor plasma conductivity throughout the treatment are used (e.g. Diascan measurements), a sodium transfer will result from the conductivity steps (10 mmol/L for 120 s for example). This sodium transfer can be either in the positive or negative direction.

Such unwanted transfers may need to be compensated for in order to maintain the desired sodium balance during the treatment.

In order to manage multiple deviations e.g. from Diascan measurements, the compensation may be implemented by integrating some, or possibly any deviation from the intended sodium set point (i.e. the sodium concentration that is set after calculation, $c_{d,M_d}$) and then compensate for this over the remaining time of treatment (T−t, where T is the total treatment time and t is the elapsed treatment time).

The applied compensated sodium concentration set point may be calculated according to the following formula:

$$c_{d,M_d,compensated} = c_{d,M_d} + \sum_i \frac{1}{T-t_i} \int_{t_i}^{t_i+\Delta t_i} (c_{d,M_d} - c_{d,Na,actual,i}) dt \quad (17)$$

where $c_{d,M_d}$ is the sodium set point calculated by the described algorithm (sodium set point which correspond to dialysis fluid concentration of sodium ions ($Na^+$) to provide the desired sodium mass transport $M_d$, cf. formula 6), $c_{d,Na,actual,i}$ is the actual dialysis fluid sodium concentration set point used during the treatment at the time an additional compensation is to be applied for (note that $c_{di,Na,actual}$ may deviate from $c_{d,M_d}$ due to both the initial estimation of isoconductivity and/or the plasma conductivity monitoring procedures, e.g. Diascan steps).

The compensation may be or may be not activated once $c_{d,M_d}$ has been calculated (for example about 15 minutes after treatment start, i.e. at the end of the identification phase), and may (or may not) take the past history into account so that any sodium transfer during the isoconductivity identification phase is also compensated.

The compensation may be applied after every sodium i-th deviation, i.e., when sodium is equal to $c_{d,Na,actual,i}$ for a duration of $\Delta t_i$. Hence, also aborted Diascan measures may be taken into account (in this case, $\Delta t$ may be lower than the forecast conductivity step).

Instead of applying a single compensation factor for each deviation, a potential alternative is to apply an integral controller, which, on the basis of the current error on applied sodium set vs. isotonic/isonatric/isonatrikalemic set found and on the time still available, applies automatically a corrected set.

The invention claimed is:

1. An apparatus for extracorporeal blood treatment comprising:
   a filtration unit including a primary chamber and a secondary chamber separated by a semi-permeable membrane;
   a blood withdrawal line connected to an inlet of the primary chamber;
   a blood return line connected to an outlet of the primary chamber, said blood lines being configured for connection to a patient cardiovascular system;
   a dialysis supply line;
   a dialysis effluent line connected to an outlet of the secondary chamber;
   a preparation device for preparing a dialysis fluid connected to said supply line and including a regulator for regulating the composition of the dialysis fluid; and
   a control unit connected to the regulator and configured to receive a set value of a parameter for the dialysis fluid in the dialysis supply line, said parameter of the dialysis fluid being at least one parameter selected from the group consisting of a conductivity of the dialysis fluid, a conductivity-related parameter of the dialysis fluid, a concentration of the substance in the dialysis fluid, and a concentration-related parameter of the substance in the dialysis fluid, and
   wherein the control unit is further configured to calculate a mass transport of a substance at an instant t of a treatment session based on said set value of the parameter for the dialysis fluid in the dialysis supply line, wherein the mass transport includes an amount of the substance that has been transported over the dialyzer membrane over a period of time.

2. The apparatus according to claim 1, wherein the control unit is further configured to:
   receive or calculate a value of a first parameter, the first parameter being chosen from a group consisting of a plasma conductivity, a plasma conductivity-related parameter, a concentration of the substance in the blood, a concentration-related parameter of the substance in the blood, and a dialysis fluid concentration of the substance at a dialysis treatment in which the substance concentration of the dialysis fluid does not change pre-filtration unit versus post-filtration unit; and
   calculate a mass transport of the substance at the instant t of the treatment session based on both said value of the first parameter and said set value of the parameter for the dialysis fluid in the dialysis supply line.

3. The apparatus according to claim 2, wherein the control unit is configured to calculate the mass transport of the substance as a function of a difference between the value of the first parameter and the set value of the parameter for the dialysis fluid in the dialysis supply line.

4. The apparatus according to claim 2, wherein the first parameter is a dialysis fluid concentration of sodium at an isonatric dialysis.

5. The apparatus according to claim 1, wherein the parameter for the dialysis fluid is a dialysis fluid concentration.

6. The apparatus according to claim 1, wherein the control unit is configured to calculate the mass transport of the substance as a function of a difference between a dialysis fluid concentration of sodium to provide isonatric dialysis and a dialysis fluid concentration set point.

7. The apparatus according to claim 1, wherein the control unit is configured to calculate the mass transport of the substance as a function of an efficiency parameter of the filtration unit for the substance.

8. The apparatus according to claim 1, wherein the control unit is configured to calculate the mass transport of the substance as a function of a respective adjusting factor taking account of the Donnan effect.

9. The apparatus according to claim 1, wherein the control unit is configured to calculate the mass transport of the substance as a function of a distribution volume of the substance.

10. The apparatus according to claim 1, wherein the control unit is configured to calculate an accumulated mass transport of the substance as a function of an elapsed treatment time.

11. The apparatus according to claim 1, wherein the control unit is configured to calculate the mass transport of the substance as a function of an ultrafiltration flow rate.

12. The apparatus according to claim 1, wherein the control unit is configured to calculate the mass transfer as a function of one or more of the following:
an efficiency parameter of the filtration unit for the substance, the efficiency parameter being the clearance of the substance,
a distribution volume of the substance,
an ultrafiltration flow rate,
a treatment time, and
a respective adjusting factor taking account of the Donnan effect.

13. The apparatus according to claim 1, wherein the first parameter is either the plasma conductivity or a dialysis fluid concentration of a substance at a dialysis treatment in which the substance concentration of the dialysis fluid does not change pre-filtration unit versus post-filtration unit, and the parameter of the dialysis fluid is the concentration of the substance in the dialysis fluid.

14. The apparatus according to claim 1, wherein the substance is sodium.

15. The apparatus according to claim 1, wherein the first parameter is a dialysis fluid concentration of sodium at an isonatric dialysis and the parameter of the dialysis fluid is the concentration of the substance in the dialysis fluid.

16. The apparatus according to claim 1, wherein the control unit is programmed for calculating a total mass transport value or a diffusive mass transport value according to the respective one of the following relationships:

total mass transport achieved at the instant t, defined as:

$$M(t) = (Q_u \cdot c_{d,set} + \delta_d \cdot K_u) \cdot t + \frac{V_0}{\alpha} \cdot (\delta_0 - \delta_d) \cdot \left(1 - \left(1 - \frac{Q_u}{V_0} \cdot t\right)^{\frac{\alpha \cdot K_u}{Q_u}}\right),$$

or diffusive mass transport achieved at the instant t, defined as:

$$M_d(t) = \left(Q_u \cdot \left(c_{d,set} - \frac{c_{d,isoNa}}{\alpha}\right) + \delta_d \cdot K_u\right) \cdot t + \frac{V_0}{\alpha} \cdot (\delta_0 - \delta_d) \cdot \left(1 - \left(1 - \frac{Q_u}{V_0} \cdot t\right)^{\frac{\alpha \cdot K_u}{Q_u}}\right)$$

wherein:

$$\delta_d = \frac{(1-\alpha) \cdot Q_u}{\alpha \cdot K_u - Q_u} \cdot c_{d,set}$$

$\delta_0 = c_{d,isoNa} - c_{d,set}$, and wherein:
M(t) is the total mass transport of sodium at the instant t,
$M_d(t)$ is the diffusive mass transport of sodium at the instant t,
$c_{d,set}$ is a dialysis fluid sodium concentration set point,
$c_{d,isoNa}$ is a dialysis fluid concentration of sodium at an isonatric dialysis,
$Q_u$ is a ultrafiltration rate,
$V_0$ is a distribution volume of sodium,
t is the instant of calculating the total mass transport value or the diffusive mass transport,
$K_u$ is a filtration unit clearance for sodium, and
$\alpha$ is a Donnan factor.

17. An apparatus for extracorporeal blood treatment comprising:
a filtration unit including a primary chamber and a secondary chamber separated by a semi-permeable membrane;
a blood withdrawal line connected to an inlet of the primary chamber;
a blood return line connected to an outlet of the primary chamber, said blood lines being configured for connection to a patient cardiovascular system;
a dialysis supply line;
a dialysis effluent line connected to an outlet of the secondary chamber;
a preparation device for preparing a dialysis fluid connected to said supply line and including a regulator for regulating the composition of the dialysis fluid; and
a control unit connected to the regulator and configured to receive a set value of a parameter for the dialysis fluid in the dialysis supply line, said parameter of the dialysis fluid being at least one parameter selected from the group consisting of a conductivity of the dialysis fluid, a conductivity-related parameter of the dialysis fluid, a concentration of the substance in the dialysis fluid, and a concentration-related parameter of the substance in the dialysis fluid, and
wherein the control unit is further configured to calculate a mass transport of a substance at an instant t of a treatment session based on said set value of the parameter for the dialysis fluid in the dialysis supply line, and wherein the control unit is programmed for calculating a total mass transport value or a diffusive mass transport value according to the respective one of the following relationships:

total mass transport achieved at the instant t, defined as:

$$M(t) = (Q_u \cdot c_{d,set} + \delta_d \cdot K_u) \cdot t + \frac{V_0}{\alpha} \cdot (\delta_0 - \delta_d) \cdot \left[1 - \left(1 - \frac{Q_u}{V_0} \cdot t\right)^{\frac{\alpha \cdot K_u}{Q_u}}\right], \text{ or}$$

diffusive mass transport achieved at the instant t, defined as:

$$M_d(t) = \left(Q_u \cdot \left(c_{d,set} - \frac{c_{d,isoNa}}{\alpha}\right) + \delta_d \cdot K_u\right) \cdot t + \frac{V_0}{\alpha} \cdot (\delta_0 - \delta_d) \cdot \left[1 - \left(1 - \frac{Q_u}{V_0} \cdot t\right)^{\frac{\alpha \cdot K_u}{Q_u}}\right]$$

wherein:

$$\delta_d = \frac{(1-\alpha) \cdot Q_u}{\alpha \cdot K_u - Q_u} \cdot c_{d,set}$$

$\delta_0 = c_{d,isoNa} - c_{d,set}$, and wherein:

M(t) is the total mass transport of sodium at the instant t, $M_d(t)$ is the diffusive mass transport of sodium at the instant t, $c_{d,set}$ is a dialysis fluid sodium concentration set point, $c_{d,isoNa}$ is a dialysis fluid concentration of sodium at an isonatric dialysis, $Q_u$ is a ultrafiltration rate, $V_0$ is a distribution volume of sodium, t is the instant of calculating the total mass transport value or the diffusive mass transport, $K_u$ is a filtration unit clearance for sodium, and α is a Donnan factor.

18. An apparatus for extracorporeal blood treatment comprising:
a filtration unit including a primary chamber and a secondary chamber separated by a semi-permeable membrane;
a blood withdrawal line connected to an inlet of the primary chamber;
a blood return line connected to an outlet of the primary chamber, said blood lines being configured for connection to a patient cardiovascular system;
a dialysis supply line;
a dialysis effluent line connected to an outlet of the secondary chamber;
a preparation device for preparing a dialysis fluid connected to said supply line and including a regulator for regulating the composition of the dialysis fluid; and
a control unit connected to the regulator and configured to receive a set value of a parameter for the dialysis fluid in the dialysis supply line, said parameter of the dialysis fluid being at least one parameter selected from the group consisting of a conductivity of the dialysis fluid, a conductivity-related parameter of the dialysis fluid, a concentration of the substance in the dialysis fluid, and a concentration-related parameter of the substance in the dialysis fluid, and wherein the control unit is further configured to:
receive or calculate a value of a first parameter, the first parameter being chosen from a group consisting of a plasma conductivity, a plasma conductivity-related parameter, a concentration of the substance in the blood, a concentration-related parameter of the substance in the blood, and a dialysis fluid concentration of the substance at a dialysis treatment in which the substance concentration of the dialysis fluid does not change pre-filtration unit versus post-filtration unit; and
calculate a mass transport of a substance at an instant t of a treatment session as a function of said set value of the parameter for the dialysis fluid in the dialysis supply line, an elapsed treatment time, an ultrafiltration flow-rate, and a difference between the value of the first parameter and the set value of the parameter for the dialysis fluid in the dialysis supply line, wherein the mass transport includes an amount of the substance that has been transported over the dialyzer membrane over a period of time.

* * * * *